US007265089B2

(12) United States Patent
Gospodarowicz et al.

(10) Patent No.: US 7,265,089 B2
(45) Date of Patent: Sep. 4, 2007

(54) KGF POLYPEPTIDE COMPOSITIONS

(75) Inventors: Denis J. Gospodarowicz, Lafayette, CA (US); W. Michael Kavanaugh, Orinda, CA (US); Kenneth Crawford, Alameda, CA (US)

(73) Assignee: Chiron Corporation, Emeryville, CA (US)

( * ) Notice: Subject to any disclaimer, the term of this patent is extended or adjusted under 35 U.S.C. 154(b) by 527 days.

(21) Appl. No.: 10/227,185

(22) Filed: Aug. 21, 2002

(65) Prior Publication Data

US 2003/0109439 A1 Jun. 12, 2003

Related U.S. Application Data

(60) Provisional application No. 60/313,881, filed on Aug. 21, 2001.

(51) Int. Cl.
*A61K 38/18* (2006.01)
*C07K 14/475* (2006.01)

(52) U.S. Cl. .............................. 514/12; 530/350; 514/2

(58) Field of Classification Search ..................... None
See application file for complete search history.

(56) References Cited

U.S. PATENT DOCUMENTS

| | | | |
|---|---|---|---|
| 5,194,596 | A | 3/1993 | Tischer et al. |
| 5,350,836 | A | 9/1994 | Kopchick et al. |
| 5,654,405 | A | 8/1997 | Rubin et al. |
| 5,665,870 | A | 9/1997 | Rubin et al. |
| 5,677,278 | A | 10/1997 | Gospodarowicz et al. |
| 5,707,805 | A | 1/1998 | Rubin et al. |
| 5,731,170 | A | 3/1998 | Rubin et al. |
| 5,741,642 | A | 4/1998 | Rubin et al. |
| 5,773,586 | A | 6/1998 | Gospodarowicz et al. |
| 5,814,605 | A | 9/1998 | Pierce et al. |
| 5,824,643 | A | 10/1998 | Pierce et al. |
| 5,843,883 | A | 12/1998 | Gospodarowicz et al. |
| 5,863,767 | A | 1/1999 | Gospodarowicz et al. |
| 5,965,530 | A | 10/1999 | Pierce et al. |
| 6,074,848 | A | 6/2000 | Gospodarowicz et al. |

FOREIGN PATENT DOCUMENTS

| | | |
|---|---|---|
| EP | 1 334 981 A2 | 8/2003 |
| WO | WO90/08771 A1 | 8/1990 |
| WO | WO95/01434 A1 | 1/1995 |
| WO | WO96/11949 A2 | 4/1996 |
| WO | WO96/11951 A2 | 4/1996 |
| WO | WO96/11952 | 4/1996 |
| WO | WO9611949 A2 * | 4/1996 |
| WO | WO98/24813 | 6/1998 |

OTHER PUBLICATIONS

Bare et al., 1994, Biochem. Biophys. Res. Commun., vol. 205, pp. 872-879.*
Ornitz and Itoh, 2001, Genome Biology, vol. 2(3), pp. 1-12.*
Osslund, et al., Protein Science, 1998, vol. 7, pp. 1681-1690.*
Nybo, et al., In Vitro Cellular and Developmental Biology: Animal, 1997, vol. 33(8), pp. 606-607.*
Nybo et al., Letter to the Editor "Mitogenic Activity of Keratinocyte Growth Factor Amino-Terminal Truncation Mutants: Deletion of Amino Acid Residues 1-15 Through 1-27", In Vitro Cell Dev. Biol., Animal 33:606-607 (1997).
Rubin et al., "Purification and Characterization of a Newly Identified Growth Factor Specific for Epithelial Cells", Proc. Natl. Acad. Sci. USA, 86:802-806 (1989).
Baird et al., "Receptor-and Heparin-Binding Domains of Basic Fibroblast Growth Factor," Proc. Natl. Acad. Sci. U.S.A. 85:2324-2328 (1988).
Basilico et al., "The FGF family of growth factors and oncogenes," Adv. Cancer Res. 59:115-165 (1992).
Bellosta et al., "Cleavage of K-FGF produces a truncated molecule with increased biological activity and receptor binding affinity," J. Cell Biol. 121(3):705-713 (1993).
Benjamin et al., "A plasticity window for blood vessel remodelling is defined by pericyte coverage of the preformed endothelial network and is regulated by PDGF-B and VEGF," Development 125:1591-1598 (1998).
Bowie et al., "Deciphering the message in protein sequences tolerance to amino acid substitutions," Science 247:1306-1310 (1990).
Burgess et al., "The Heparin-Binding (Fibroblast) Growth Factor Family of Proteins," Anan. Rev. Biochem. 58:575-605 (1989).
Curti, "Physical barriers to drug delivery in tumors," Critical Reviews in Oncology/Hematology 14:29-39 (1993).
Eriksson et al., "Three-Dimensional Structure of Human Basic Fibroblast Growth Factor," Proc. Natl. Acad. Sci. U.S.A. 88:3441-3445 (1991).
Finch et al., "Human KGF is FGF-related with properties of a paracrine effector of epithelial cell growth," Science 245:752-755 (1989).
Gospodarowicz et al., "Comparison of the Ability of Basic and Acidic Fibroblast Growth Factor to Stimulate the Proliferation of an Established Keratinocyte Cell Line: Modulation of Their Biological Effects by Heparin, Transforming Growth Factor β (TGFβ), and Epidermal Growth Factor (EGF)," Journal of Cellular Physiology 142:325-333 (1990).
Gospodarowicz et al., "Fibroblast growth factors: from genes to clinical applications," Cell. Biol. Rev. 25:307-314 (1991).
Harper et al., "Reductive Methylation of Lysine Residues in Acidic Fibroblast Growth Factor: Effect on Mitogenic Activity and Heparin Affinity," Biochemistry 27:671-678 (1988).
Jain, "Barriers to drug delivery in solid tumors," Scientific American 271:58-65 (1994).

(Continued)

*Primary Examiner*—Eileen B. O'Hara
*Assistant Examiner*—Xiaozhen Xie
(74) *Attorney, Agent, or Firm*—Susan L. Abrahamson; Roberta L. Robins; Alisa A. Harbin

(57) ABSTRACT

Compositions comprising keratinocyte growth factor (KGF) polypeptides and methods of using the same are described. The KGF polypeptides of the present invention display enhanced bioactivity relative to full-length $KGF_{163}$. Accordingly, the KGF polypeptides of the present invention may be used in compositions in lesser amounts than would be necessary using $KGF_{163}$.

19 Claims, 9 Drawing Sheets

OTHER PUBLICATIONS

Massague, "The TGF- family of growth and differentiation factors," *Cell* 49:437-438 (1987).

Meyer-Ingold "Wound therapy: growth factors as agents to promote healing," *Tibtech* 11:387-392 (1993).

Ngo et al., "Computational Complexity, Protein Structure Prediction, and the Levinthal paradox," in *The Protein Folding Problem and Tertary Structure Prediction*, Merz et al., eds., Birkhauser, Boston, pp. 491-495 (1994).

Osslund et al., "Correlation Between the 1.6 Å Crystal Structure and Mutational Analysis of Keratinocyte Growth Factor," *Protein Science* 7:1681-1690 (1998).

Pilbeam et al., "Comparison of the effects of various lengths of synthetic human parathyroid hormone-related peptide (hPTHrP) of malignancy on bone resorption and formation in organ culture," *Bone* 14:717-720 (1993).

Powers et al., "Fibroblast growth factors, their receptors and signaling," *Endocrine-Related Cancer* 7:165-197 (2000).

Reich-Slotky et al., "Chimeric Molecules Between Keratinocyte Growth Factor and Basic Fibroblast Growth Factor Define Domains that Confer Receptor Binding Specificities," *The Journal of Biological Chemistry* 270(50):29813-29818.

Robinson, "Growth factors in wound healing," *Tibtec* 10:1-2 (1992).

Ron et al. "Expression of biologically active recombinant keratinocyte growth factor," *J. Biol Chem.* 268(4):2984-2988 (1993).

Vukicevic et al., "Induction of nephrogenic mesenchyme by osteogenic protein 1 (bone morphogenetic protein 7)," *PNAS USA* 93:9021-9026 (1996).

Wells, "Additivity of mutational effects in proteins," *Biochemistry* 29:8509-8517 (1990).

* cited by examiner

```
      C   N   D   M   T   P   E   Q   M   A   T   N   V   N
                                  10
     TGC AAT GAC ATG ACT CCA GAG CAA ATG GCT ACA AAT GTG AAC

20
      C   S   S   P   E   R   H   T   R   S   Y   D   Y   M   E
     TGT TCC AGC CCT GAG CGA CAC ACA AGA AGT TAT GAT TAC ATG GAA 30                                          40
      G   G   D   I   R   V   R   R   L   F   C   R   T   Q   W
     GGA GGG GAT ATA AGA GTG AGA AGA CTC TTC TGT CGA ACA CAG TGG

50
      Y   L   R   I   D   K   R   G   K   V   K   G   T   Q   E
     TAC CTG AGG ATC GAT AAA AGA GGC AAA GTA AAA GGG ACC CAA GAG 60                                                  70
      M   K   N   N   Y   N   I   M   E   I   R   T   V   A   V
     ATG AAG AAT AAT TAC AAT ATC ATG GAA ATC AGG ACA GTG GCA GTT

80
      G   I   V   A   I   K   G   V   E   S   E   F   Y   L   A
     GGA ATT GTG GCA ATC AAA GGG GTG GAA AGT GAA TTC TAT CTT GCA 90                                              100
      M   N   K   E   G   K   L   Y   A   K   K   E   C   N   E
     ATG AAC AAG GAA GGA AAA CTC TAT GCA AAG AAA GAA TGC AAT GAA

110
      D   C   N   F   K   E   L   I   L   E   N   H   Y   N   T
     GAT TGT AAC TTC AAA GAA CTA ATT CTG GAA AAC CAT TAC AAC ACA 120                                                 130
      Y   A   S   A   K   W   T   H   N   G   E   M   F   V
     TAT GCA TCA GCT AAA TGG ACA CAC AAC GGA GGG GAA ATG TTT GTT

140
      A   L   N   Q   K   G   I   P   V   R   G   K   K   T   K
     GCC TTA AAT CAA AAG GGG ATT CCT GTA AGA GGA AAA AAA ACG AAG 150                                         160         163
      K   E   Q   K   T   A   H   F   L   P   M   A   I   T
     AAA GAA CAA AAA ACA GCC CAC TTT CTT CCT ATG GCA ATA ACT
```

*FIG. 1*

```
GCT AGT TAT GAT TAC ATG GAA GGA GGG GAT ATA AGA GTG AGA AGA
 A   S   Y   D   Y   M   E   G   G   D   I   R   V   R   R

CTC TTC TGT CGA ACA CAG TGG TAC CTG AGG ATC GAT AAA AGA GGC
 L   F   C   R   T   Q   W   Y   L   R   I   D   K   R   G

AAA GTA AAA GGG ACC CAA GAG ATG AAG AAT AAT TAC AAT ATC ATG
 K   V   K   G   T   Q   E   M   K   N   N   Y   N   I   M

GAA ATC AGG ACA GTG GCA GTT GGA ATT GTG GCA ATC AAA GGG GTG
 E   I   R   T   V   A   V   G   I   V   A   I   K   G   V

GAA AGT GAA TTC TAT CTT GCA ATG AAC AAG GAA GGA AAA CTC TAT
 E   S   E   F   Y   L   A   M   N   K   E   G   K   L   Y

GCA AAG AAA GAA TGC AAT GAA GAT TGT AAC TTC AAA GAA CTA ATT
 A   K   K   E   C   N   E   D   C   N   F   K   E   L   I

CTG GAA AAC CAT TAC AAC ACA TAT GCA TCA GCT AAA TGG ACA CAC
 L   E   N   H   Y   N   T   Y   A   S   A   K   W   T   H

AAC GGA GGG GAA ATG TTT GTT GCC TTA AAT CAA AAG GGG ATT CCT
 N   G   G   E   M   F   V   A   L   N   Q   K   G   I   P

GTA AGA GGA AAA AAA ACG AAG AAA GAA CAA AAA ACA GCC CAC TTT
 V   R   G   K   K   T   K   K   E   Q   K   T   A   H   F

CTT CCT ATG GCA ATA ACT
 L   P   M   A   I   T
```

FIG. 8

KGF POLYPEPTIDE COMPOSITIONS

CROSS REFERENCE TO RELATED APPLICATIONS

This application claims the benefit of provisional patent application Ser. No. 60/313,881, filed Aug. 21, 2001, pursuant to 35 USC §119(e)(1), which application is incorporated herein by reference in its entirety.

TECHNICAL FIELD

The present invention relates generally to polypeptide growth factors. Specifically, the invention relates to compositions comprising keratinocyte growth factor polypeptides and methods of using the same.

BACKGROUND OF THE INVENTION

Keratinocyte growth factor (KGF) belongs to the family of fibroblast growth factors ("FGFs"), the prototypes of which are represented by basic FGF and acidic FGF. KGF is also known as FGF-7. KGF, like FGFs, binds heparin and is generally capable of stimulating the proliferation and differentiation of a variety of cell types derived from the primary or secondary mesoderm as well as from neuroectoderm. For example, KGF, like FGFs, has the ability to induce the differentiation and proliferation of ventral as well as dorsal mesoderm in early blastulae. See, e.g., Gospodarowicz et. al. *Cell. Biol. Rev.* (1991) 25:307-314; and Basilico et al. *Adv. Cancer Res.* (1992) 59:115-165.

Like other FGFs, KGF is a heparin-binding protein, but unlike other FGFs, it has a unique target cell specificity. Particularly, KGF is similar to other FGFs in its ability to stimulate epithelial cell proliferation, but is dissimilar to other FGFs in its inability to stimulate endothelial cells or fibroblast proliferation. See, e.g., Finch, et. al. *Science* (1989) 245: 752-755. Mature, full-length KGF, designated herein as $KGF_{163}$, is a polypeptide with 163 amino acid residues, and possesses a potential N-glycosylation site that extends from amino acid residue 14 to 16 at the N-terminus. Finch, et. al. *Science* (1989) 245: 752-755.

Ron et al. *J. Biol. Chem.* (1993) 268:2984-2988 found that when $KGF_{163}$ was expressed in a prokaryotic expression system, a recombinant KGF ("rKGF") polypeptide could be obtained that possessed mitogenic activity. When the rKGF molecule was truncated by deletion of 3, 8, 27, 38, and 48 amino acid residues from the N-terminus of the mature $KGF_{163}$ polypeptide, biological activity of the resulting molecules varied. With deletion of 3 and 8 amino acid residues, respectively, the mitogenic activity of the resulting molecules did not appear to be affected as compared to full-length rKGF. Deletion of 27 amino acid residues, however, resulted in molecules that displayed 10-20 fold reduced mitogenic activity. Deletion of 38 and 48 amino acid residues, respectively, resulted in complete loss of mitogenic activity and heparin-binding ability. Ron et al., however, failed to produce any truncated rKGF fragments that possessed increased mitogenic activity as compared to the full-length rKGF molecule.

U.S. Pat. Nos. 5,677,278, 5,773,586, 5,843,883, 5,863,767 and 6,074,848, all to Gospodarowicz et al., describe KGF molecules. One particular molecule, with an N-terminal deletion of 23 amino acid residues, termed $KGF_{des1-23}$, demonstrates enhanced mitogenic activity as compared to mature, full-length recombinant $KGF_{163}$.

Osslund et al. *Protein Sci.* (1998) 7:1681-1690 reports various N-terminal truncated KGF molecules and certain measurements of their mitogenic activity. Similarly, International Publications WO 96/11951 and WO 96/11949 describe KGF molecules with various N-terminal truncations and amino acid substitutions.

DISCLOSURE OF THE INVENTION

The present invention is based on the discovery that various N-terminally truncated KGF polypeptides, and analogs thereof, display enhanced biological activity on a per molecule basis relative to native, full-length $KGF_{163}$. Thus, compositions containing these molecules have increased potency for the treatment of conditions where epithelialization is required, such as for the treatment of wounds, burns, ophthalmic disorders, gastrointestinal diseases and any disorder where stimulation of epithelial cell proliferation or regeneration is desired. These molecules can be delivered alone or in combination with other mitogenic agents, such as other growth factors, including for example, any of the other FGFs, as well as platelet derived growth factor (PDGF), epidermal growth factor (EGF), insulin-like growth factor (IGF), insulin-like growth factor binding proteins (IGFBPs), and the like.

Moreover, these KGF molecules can be conjugated to toxin molecules in order to target these toxins to epithelial cells in order to treat hyperproliferative diseases.

Accordingly, in one embodiment, the subject invention is directed to a method of stimulating epithelial cell proliferation. The method comprises contacting epithelial cells with a composition comprising:

(a) a therapeutically effective amount of a KGF polypeptide, wherein the KGF polypeptide is selected from the group consisting of:

(i) $KGF_{des1-25}$ consisting of the contiguous amino acid sequence depicted at amino acid residues 16-163, inclusive, of FIG. 1;

(ii) $KGF_{des1-18}$ consisting of the contiguous amino acid sequence depicted at amino acid residues 19-163, inclusive, of FIG. 1;

(iii) $KGF_{des1-19}$ consisting of the contiguous amino acid sequence depicted at amino acid residues 20-163, inclusive, of FIG. 1;

(iv) $KGF_{des1-20}$ consisting of the contiguous amino acid sequence depicted at amino acid residues 21-163, inclusive, of FIG. 1;

(v) $KGF_{des1-21}$ consisting of the contiguous amino acid sequence depicted at amino acid residues 22-163, inclusive, of FIG. 1;

(vi) $KGF_{des1-22}$ consisting of the contiguous amino acid sequence depicted at amino acid residues 23-163, inclusive, of FIG. 1;

(vii) $KGF_{des1-24}$ consisting of the contiguous amino acid sequence depicted at amino acid residues 25-163, inclusive, of FIG. 1;

(viii) $KGF_{des1-25}$ consisting of the contiguous amino acid sequence depicted at amino acid residues 26-163, inclusive, of FIG. 1;

(ix) a biologically active analog of (i), (ii), (iii), (iv), (v), (vi), (vii) or (viii), wherein the biologically active analog consists of the same number of amino acids as (i), (ii), (iii), (iv), (v), (vi), (vii) or (viii), respectively, and has at least 70% sequence homology thereto;

wherein the KGF polypeptide exhibits an increase in bioactivity relative to mature, full-length, KGF ($KGF_{163}$) as determined by the Balb/MK bioactivity assay and specifically stimulates epithelial cell proliferation, and further wherein the therapeutically effective amount is 75% or less of the amount on a per molecule basis of $KGF_{163}$ needed to elicit an equivalent therapeutic response; and (b) a pharmaceutically acceptable excipient.

In certain embodiments, the biologically active analog has at least 80% or 90% sequence homology to (i), (ii), (iii), (iv), (v), (vi), (vii), (viii) or (ix).

In another embodiment, the invention is directed to a method as described above wherein the KGF polypeptide is $KGF_{des1-22}$ consisting of the contiguous amino acid sequence depicted at amino acid residues 23-163, inclusive, of FIG. 1, or a biologically active analog thereof wherein the biologically active analog consists of 141 amino acids and has at least 70% sequence homology thereto, and wherein the therapeutically effective amount is 50% or less of the amount on a per molecule basis of $KGF_{163}$ needed to elicit an equivalent therapeutic response.

In yet further embodiments, the invention is directed to a method as described above wherein the KGF polypeptide is $KGF_{des1-24}$ consisting of the contiguous amino acid sequence depicted at amino acid residues 25-163, inclusive, of FIG. 1, or a biologically active analog thereof wherein the biologically active analog consists of 139 amino acids and has at least 70% sequence homology thereto, and wherein the therapeutically effective amount is 50% or less of the amount on a per molecule basis of $KGF_{163}$ needed to elicit an equivalent therapeutic response.

In a further embodiment, the invention is directed to a method of stimulating epithelial cell proliferation which comprises contacting epithelial cells with a composition comprising:

a) a therapeutically effective amount of a KGF polypeptide, wherein the KGF polypeptide is (i) $KGF_{des1-22}$ consisting of the contiguous amino acid sequence depicted at amino acid residues 23-163, inclusive, of FIG. 1, or (ii) a biologically active analog of (i) which consists of the same number of amino acids as (i) and has at least 70% sequence homology thereto, wherein the KGF polypeptide exhibits an increase in bioactivity relative to mature, full-length, KGF ($KGF_{163}$) as determined by the Balb/MK bioactivity assay and specifically stimulates epithelial cell proliferation, and further wherein the therapeutically effective amount is 10% to 75% of the amount on a per molecule basis of $KGF_{163}$ needed to elicit an equivalent therapeutic response; and (b) a pharmaceutically acceptable excipient.

In certain embodiments, the biologically active analog has at least 80% or 90% sequence homology to (i) or (ii).

In other embodiments, the biologically active analog consists of the contiguous amino acid sequence depicted at amino acid residues 23-163, inclusive, of FIG. 1 with the N-terminal arginine residue substituted with an alanine residue.

In still further embodiments, the therapeutically effective amount is 10% to 20%, or 10% to 25%, or 10% to 50% of the amount on a per molecule basis, or any percentage within these ranges, of the amount of full-length KGF needed to elicit an equivalent therapeutic response.

In another embodiment, the invention is directed to a method of stimulating epithelial cell proliferation comprising contacting epithelial cells with a composition comprising:

a) a therapeutically effective amount of a KGF polypeptide, wherein the KGF polypeptide is (i) $KGF_{des1-24}$ consisting of the contiguous amino acid sequence depicted at amino acid residues 25-163, inclusive, of FIG. 1, or (ii) a biologically active analog of (i) which consists of the same number of amino acids as (i) and has at least 70% sequence homology thereto, wherein the KGF polypeptide exhibits an increase in bioactivity relative to mature, full-length, KGF ($KGF_{163}$) as determined by the Balb/MK bioactivity assay and specifically stimulates epithelial cell proliferation, and further wherein the therapeutically effective amount is 5% to 75% of the amount on a per molecule basis of $KGF_{163}$ needed to elicit an equivalent therapeutic response; and (b) a pharmaceutically acceptable excipient.

In certain embodiments of the method described above, the biologically active analog has at least 80% or at least 90% sequence homology to (i) or (ii).

In additional embodiments, the therapeutically effective amount is 5% to 10%, 10% to 20%, 10% to 25%, or 10% to 50%, or any percentage within these ranges, of the amount on a per molecule basis of the amount of full-length KGF needed to elicit an equivalent therapeutic response.

In all of the methods described above, epithelial cells may be contacted with the KGF polypeptides in vitro or in vivo.

In another embodiment, the invention is directed to a method of treating wounds comprising applying a KGF polypeptide composition to an area of a wound to be treated and allowing the wound to heal. The composition comprises:

(a) a therapeutically effective amount of a KGF polypeptide, wherein the KGF polypeptide is selected from the group consisting of:

(i) $KGF_{des1-15}$ consisting of the contiguous amino acid sequence depicted at amino acid residues 16-163, inclusive, of FIG. 1;

(ii) $KGF_{des1-18}$ consisting of the contiguous amino acid sequence depicted at amino acid residues 19-163, inclusive, of FIG. 1;

(iii) $KGF_{des1-19}$ consisting of the contiguous amino acid sequence depicted at amino acid residues 20-163, inclusive, of FIG. 1;

(iv) $KGF_{des1-20}$ consisting of the contiguous amino acid sequence depicted at amino acid residues 21-163, inclusive, of FIG. 1;

(v) $KGF_{des1-21}$ consisting of the contiguous amino acid sequence depicted at amino acid residues 22-163, inclusive, of FIG. 1;

(vi) $KGF_{des1-22}$ consisting of the contiguous amino acid sequence depicted at amino acid residues 23-163, inclusive, of FIG. 1;

(vii) $KGF_{des1-24}$ consisting of the contiguous amino acid sequence depicted at amino acid residues 25-163, inclusive, of FIG. 1;

(viii) $KGF_{des1-25}$ consisting of the contiguous amino acid sequence depicted at amino acid residues 26-163, inclusive, of FIG. 1;

(ix) a biologically active analog of (i), (ii), (iii), (iv), (v), (vi), (vii) or (viii), wherein the biologically active analog consists of the same number of amino acids as (i), (ii), (iii), (iv), (v), (vi), (vii) or (viii), respectively, and has at least 70% sequence homology thereto, wherein the KGF polypeptide exhibits an increase in bioactivity relative to mature, full-length, KGF ($KGF_{163}$) as determined by the Balb/MK bioactivity assay and specifically stimulates epithelial cell proliferation, and further wherein the therapeutically effective amount is 75% or less of the amount on a per molecule basis of $KGF_{163}$ needed to elicit an equivalent therapeutic response; and (b) a pharmaceutically acceptable excipient.

In certain embodiments of the above method, the biologically active analog has at least 80% or 90% sequence homology to (i), (ii), (iii), (iv), (v), (vi), (vii), (viii) or (ix).

In additional embodiments of the above method, the KGF polypeptide is $KGF_{des1-22}$ consisting of the contiguous amino acid sequence depicted at amino acid residues 23-163, inclusive, of FIG. 1, or a biologically active analog thereof wherein the biologically active analog consists of 141 amino acids and has at least 70% sequence homology thereto, and wherein the therapeutically effective amount is 50% or less of the amount on a per molecule basis of $KGF_{163}$ needed to elicit an equivalent therapeutic response.

In other embodiments of the above method, the KGF polypeptide is $KGF_{des1-24}$ consisting of the contiguous amino acid sequence depicted at amino acid residues 25-163, inclusive, of FIG. 1, or a biologically active analog thereof wherein the biologically active analog consists of 139 amino acids and has at least 70% sequence homology thereto, and wherein the therapeutically effective amount is 50% or less of the amount on a per molecule basis of $KGF_{163}$ needed to elicit an equivalent therapeutic response.

In still further embodiments, the invention is directed to a method of treating wounds comprising applying a KGF polypeptide composition to an area of a wound to be treated and allowing the wound to heal, said composition comprising:

a) a therapeutically effective amount of a KGF polypeptide, wherein the KGF polypeptide is (i) $KGF_{des1-22}$ consisting of the contiguous amino acid sequence depicted at amino acid residues 23-163, inclusive, of FIG. 1, or (ii) a biologically active analog of (i) which consists of the same number of amino acids as (i) and has at least 70% sequence homology thereto, wherein the KGF polypeptide exhibits an increase in bioactivity relative to mature, full-length, KGF ($KGF_{163}$) as determined by the Balb/MK bioactivity assay and specifically stimulates epithelial cell proliferation, and further wherein the therapeutically effective amount is 10% to 75% of the amount on a per molecule basis of $KGF_{163}$ needed to elicit an equivalent therapeutic response; and (b) a pharmaceutically acceptable excipient.

In certain embodiments, the biologically active analog has at least 80% sequence homology or at least 90% sequence homology to (i) or (ii).

In additional embodiments of the method above, the biologically active analog consists of the contiguous amino acid sequence depicted at amino acid residues 23-163, inclusive, of FIG. 1 with the N-terminal arginine residue substituted with an alanine residue.

In still further embodiments, the therapeutically effective amount for use in the methods above is 10% to 20%, or 10% to 25%, or 10% to 50% of the amount on a per molecule basis, or any percentage within these ranges, of the amount of full-length KGF needed to elicit an equivalent therapeutic response.

In additional embodiments, the invention is directed to a method of treating wounds comprising applying a KGF polypeptide composition to an area of a wound to be treated and allowing the wound to heal, said composition comprising:

a) a therapeutically effective amount of a KGF polypeptide, wherein the KGF polypeptide is (i) $KGF_{des1-24}$ consisting of the contiguous amino acid sequence depicted at amino acid residues 25-163, inclusive, of FIG. 1, or a biologically active analog of (i) which consists of the same number of amino acids as (i) and has at least 70% sequence homology thereto, wherein the KGF polypeptide exhibits an increase in bioactivity relative to mature, full-length, KGF ($KGF_{163}$) as determined by the Balb/MK bioactivity assay and specifically stimulates epithelial cell proliferation, and further wherein the therapeutically effective amount is 5% to 75% of the amount on a per molecule basis of $KGF_{163}$ needed to elicit an equivalent therapeutic response; and (b) a pharmaceutically acceptable excipient.

In certain embodiments of the above method, the biologically active analog has at least 80% sequence homology or at least 90% sequence homology to (i) or (ii).

In still further embodiments, the therapeutically effective amount for use in the method above is 5% to 10%, or 10% to 20%, or 10% to 25%, or 10% to 50% of the amount on a per molecule basis, or any percentage within these ranges, of the amount of full-length KGF needed to elicit an equivalent therapeutic response.

In the above methods, the composition may be contacted with the wound in vitro or in vivo.

In yet further embodiments, the invention is directed to a composition comprising:

(a) a therapeutically effective amount of a KGF polypeptide, wherein the KGF polypeptide is selected from the group consisting of:
  (i) $KGF_{des1-15}$ consisting of the contiguous amino acid sequence depicted at amino acid residues 16-163, inclusive, of FIG. 1;
  (ii) $KGF_{des1-18}$ consisting of the contiguous amino acid sequence depicted at amino acid residues 19-163, inclusive, of FIG. 1;
  (iii) $KGF_{des1-19}$ consisting of the contiguous amino acid sequence depicted at amino acid residues 20-163, inclusive, of FIG. 1;
  (iv) $KGF_{des1-20}$ consisting of the contiguous amino acid sequence depicted at amino acid residues 21-163, inclusive, of FIG. 1;
  (v) $KGF_{des1-21}$ consisting of the contiguous amino acid sequence depicted at amino acid residues 22-163, inclusive, of FIG. 1;
  (vi) $KGF_{des1-22}$ consisting of the contiguous amino acid sequence depicted at amino acid residues 23-163, inclusive, of FIG. 1;
  (vii) $KGF_{des1-24}$ consisting of the contiguous amino acid sequence depicted at amino acid residues 25-163, inclusive, of FIG. 1;
  (viii) $KGF_{des1-25}$ consisting of the contiguous amino acid sequence depicted at amino acid residues 26-163, inclusive, of FIG. 1;
  (ix) a biologically active analog of (i), (ii), (iii), (iv), (v), (vi), (vii) or (viii), wherein said biologically active analog consists of the same number of amino acids as (i), (ii), (iii), (iv), (v), (vi), (vii) or (viii), respectively, and has at least 70% sequence homology thereto; and
  (x) an analog of (i), (ii), (iii), (iv), (v), (vi), (vii), (viii) or (ix), consisting of the amino acid sequence of (i), (ii), (iii), (iv), (v), (vi), (vii), (viii) or (ix), respectively, and an additional N-terminal methionine, wherein the KGF polypeptide exhibits an increase in bioactivity relative to mature, full-length, KGF ($KGF_{163}$) as determined by the Balb/K bioactivity assay and specifically stimulates epithelial cell proliferation, and further wherein the therapeutically effective amount is 75% or less of the amount on a per molecule basis of $KGF_{163}$ needed to elicit an equivalent therapeutic response; and (b) a pharmaceutically acceptable excipient.

In certain embodiments, the biologically active analog has at least 80% sequence homology or at least 90% sequence homology to (i), (ii), (iii), (iv), (v), (vi), (vii), (viii) or (ix).

These and other aspects of the present invention will become evident upon reference to the following detailed description and attached figures. In addition, various references are set forth herein which describe in more detail certain procedures or compositions, and are therefore incorporated by reference in their entirety.

BRIEF DESCRIPTION OF THE FIGURES

FIG. 1 (SEQ ID NOS: 25 and 26) depicts the DNA sequence and corresponding amino acid sequence for mature, full-length KGF ($KGF_{163}$).

FIG. 2A compares activity of $KGF_{des1-22}$ (◆), $KGF_{des1-23}$ (■), $KGF_{des1-24}$ (▲) $KGF_{des1-26}$ (×) and $KGF_{des1-30}$ (double ×), while FIG. 2B shows a comparison of $KGF_{des1-23}$ (■), $KGF_{des1-26}$ (×) and $KGF_{des1-30}$ (double ×) with acidic FGF (aFGF, ◆, middle line) and full-length KGF (FL-KGF, (◆, second to the top line).

FIG. 8 (SEQ ID NOS:27 and 28) shows the DNA sequence and corresponding amino acid sequence for $KGF_{des1-22}$, with the N-terminal arginine residue substituted with an alanine residue.

DETAILED DESCRIPTION OF THE INVENTION

Figure 2A:
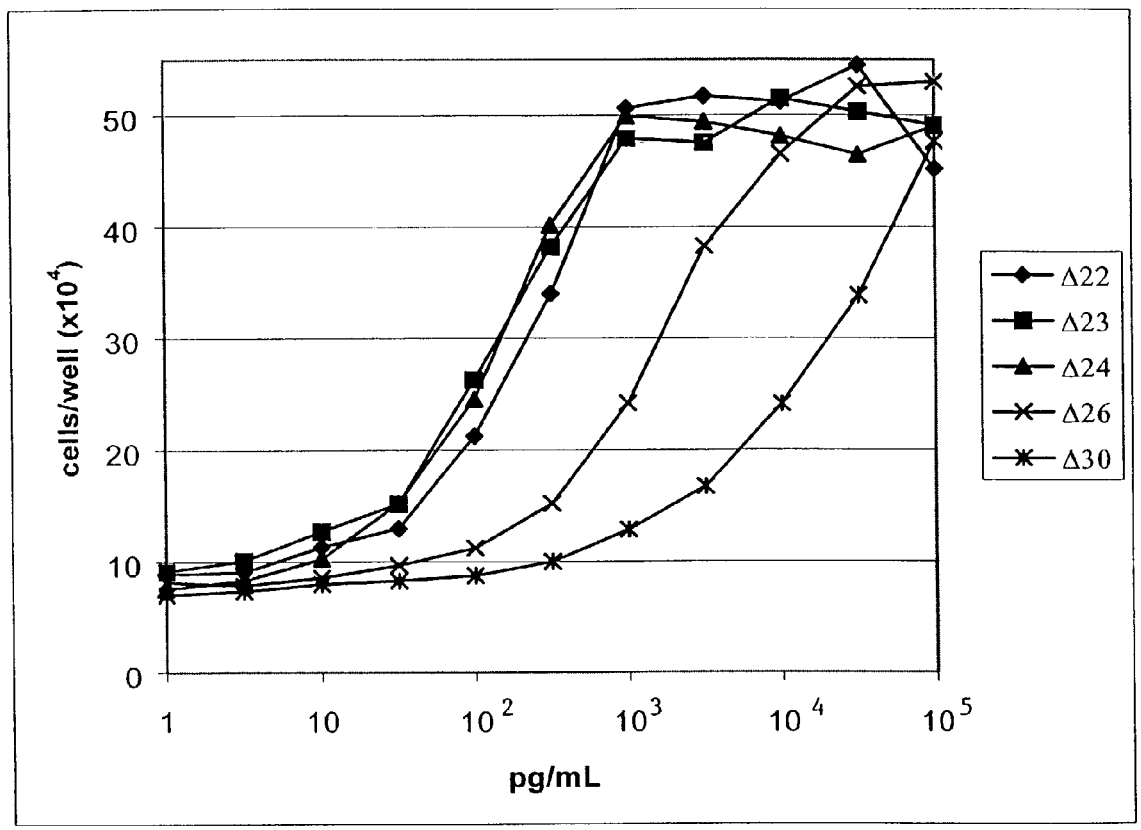
FIGS. 2A and 2B show a comparison of the biological activity of various N-terminally truncated KGF polypeptides.

The practice of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, *Proteins: Structures and Molecular Properties* (W.H. Freeman and Company, 1993); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.); *Remington's Pharmaceutical Sciences*, 18th Edition (Easton, Pa.: Mack Publishing Company, 1990).

All publications, patents and patent applications cited herein, whether supra or infra, are hereby incorporated by reference in their entirety.

The following amino acid abbreviations are used throughout the text:

| | |
|---|---|
| Alanine: Ala (A) | Arginine: Arg (R) |
| Asparagine: Asn (N) | Aspartic acid: Asp (D) |
| Cysteine: Cys (C) | Glutamine: Gln (Q) |
| Glutamic acid: Glu (E) | Glycine: Gly (G) |
| Histidine: His (H) | Isoleucine: Ile (I) |
| Leucine: Leu (L) | Lysine: Lys (K) |
| Methionine: Met (M) | Phenylalanine: Phe (F) |
| Proline: Pro (P) | Serine: Ser (S) |
| Threonine: Thr (T) | Tryptophan: Trp (W) |
| Tyrosine: Tyr (Y) | Valine: Val (V) |

I. DEFINITIONS

In describing the present invention, the following terms will be employed, and are intended to be defined as indicated below.

The terms "polypeptide" and "protein" refer to a polymer of amino acid residues and are not limited to a minimum length of the product. The terms also include, unless otherwise indicated, modifications of the polypeptide that do not change the sequence of amino acids, for example, glycosylated, acetylated and phosphorylated forms. A polypeptide or protein, for purposes of the present invention, may be synthetically or recombinantly produced, as well as isolated from natural sources.

As used herein, the term "keratinocyte growth factor" or "KGF" refers to a member of a group of the FGF family of proteins which is capable of binding to FGFR-2, lacks significant activity on fibroblasts, is uniquely specific for epithelial cells and is particularly active on keratinocytes. KGF, analogs and fragments thereof (defined below) may be synthetically or recombinantly produced. Moreover, KGF may be isolated from natural sources, such as from any of several tissues of any mammalian source, for example from human tissues.

"Mature, full-length KGF," "long form of KGF," "FL-KGF," "native KGF" or "$KGF_{163}$" as used herein all refer to the mature polypeptide that contains 163 amino acid residues, as shown in FIG. 1.

As used herein, the term "KGF fragment" refers to a polypeptide derived from $KGF_{163}$ that does not include the entire sequence of $KGF_{163}$. Such a fragment may be a truncated version of the full-length molecule, as well as an internally deleted polypeptide. A KGF fragment may have KGF bioactivity as determined by the Balb/K bioactivity assay, described in Example 4 herein. The Balb/MK cell line (Weissman, B. E. and Aaronson, S. A. *Cell* (1983) 32:599-606) is a clonal Balb/c mouse keratinocyte cell line. These cells are dependent for their growth upon an exogenous source of an epithelial cell mitogen even in medium containing serum. Thus, activity of the KGF fragments and analogs is measured by determining the $ED_{50}$ value using Balb/Mk cells, said value defined by the concentration of KGF fragment that causes half maximal stimulation of cell proliferation. Additionally, the KGF fragments of the invention specifically stimulate epithelial cell proliferation.

To determine target cell specificity, DNA synthesis stimulation, expressed as the ratio of stimulated synthesis over background incorporation of thymidine in the absence of added test sample, is compared to analogous stimulation observed in cells other than keratinocytes under the same assay conditions. The activity of the KGF fragments and analogs can also be tested on endothelial cells, such as adult bovine aortic endothelial cells (ABAE) or adrenal cortex-derived capillary endothelial cells (ACE), as described in Example 5 herein. A KGF polypeptide or analog that "specifically stimulates epithelial cell proliferation" may be a molecule that, at saturating concentrations, (i) in the Balb/Mk assay described in Example 4 herein, can stimulate the final cell number per well after 7 days in culture to a level at least 4-fold higher than the cell number achieved in wells receiving no KGF; and (ii) in the ABAE or ACE assay described in Example 5 herein, does not significantly stimulate the final cell number per well after 7 days in culture to a level higher than the cell number achieved in wells receiving no KGF.

U.S. Pat. No. 5,731,170, incorporated by reference herein in its entirety, reports that certain molecules display KGF mitogenic activity with marked specificity for keratinocytes as opposed to fibroblasts.

The fragments of the present invention will display enhanced activity on a per molecule basis relative to $KGF_{163}$, such as anywhere from 10% or more activity, such as 15%, 20%, 25%, 50%, 100% or more, to as much as 10-fold or more activity, or any amount between the specified ranges. Hence, the KGF fragments of the present invention may be used in compositions in lesser amounts than would be necessary using $KGF_{163}$. The inventors herein recognize that truncations produce molecules of lower molecular weight than full-length KGF. As shown below in the Examples, these species are more active when compared on a per molecule basis (i.e., when activity is adjusted for the molecular weight). Particular KGF fragments are described in detail below.

The term "analog" refers to derivatives of the reference molecule. The analog may retain biological activity, as described above. In general, the term "analog" refers to compounds having a native polypeptide sequence and structure with one or more amino acid additions, substitutions (generally conservative in nature) and/or deletions, relative to the native molecule, so long as the modifications do not destroy activity. Preferably, the analog has at least the same biological activity as the parent molecule, and may even display enhanced activity over the parent molecule. Methods for making polypeptide analogs are known in the art and are described further below.

Particularly preferred analogs include substitutions that are conservative in nature, i.e., those substitutions that take place within a family of amino acids that are related in their side chains. Specifically, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cysteine, serine, threonine, tyrosine. Phenylalanine, tryptophan, and tyrosine are sometimes classified as aromatic amino acids. For example, it is reasonably predictable that an isolated replacement of leucine with isoleucine or valine, an aspartate with a glutamate, a threonine with a serine, or a similar conservative replacement of an amino acid with a structurally related amino acid, will not have a major effect on the biological activity. For example, the polypeptide of interest may include up to about 1-70 conservative or non-conservative amino acid substitutions, such as 1, 2, 3, 4, 5-50, 15-25, 5-10, or any integer between 1-70, so long as the desired function of the molecule remains intact. One of skill in the art may readily determine regions of the molecule of interest that can be modified with a reasonable likelihood of retaining biological activity as defined herein.

For example, none of the critical determinants involved in signaling appear to be located within the first 30 N-terminal amino acids of KGF (Plotnikov, et. al. *Cell* (2000) 101:413-424). Additionally, the $NH_2$ terminal domain of KGF does not appear to be involved in its cell specificity. Amino acid residues 91-110, numbered relative to the amino acid sequence set forth in FIG. 1 appear to confer receptor binding specificity to KGF (Reich-Slotsky, et al. *J. Biol. Chem.* (1995) 270:29813-29818). Thus, analogs and fragments which retain the region spanning at least amino acids 91-110 are preferred. Moreover, if amino acid substitutions are made in this region, they should be conservative in nature. Fragments which retain portions of the N-terminal sequence, e.g., fragments with deletions that do not extend to, for example, amino acid 35, numbered relative to FIG. 1, are more tolerable to amino acid additions, deletions and substitutions. Preferred deletions include deletions of the first 22, 23 and 24 amino acids, as described further below. One of skill in the art can readily determine other regions that will tolerate change based on the known structure of KGF (see, e.g., Osslund et al. *Protein Sci.* (1998) 7:1681-1690), as well as the known structure/function relationships between KGF and related molecules such as acidic FGF, basic FGF and kaposi FGF (see, e.g., Gospodarowicz et al., *J. Cell. Physiol.* (1990) 142:325-333).

By "purified" and "isolated" is meant, when referring to a polypeptide or polynucleotide, that the indicated molecule is present in the substantial absence of other biological macromolecules of the same type. The term "purified" as used herein preferably means at least 75% by weight, more preferably at least 85% by weight, more preferably still at least 95% by weight, and most preferably at least 98% by weight, of biological macromolecules of the same type are present in the sample. An "isolated polynucleotide which encodes a particular polypeptide" refers to a nucleic acid molecule which is substantially free of other nucleic acid molecules that do not encode the subject polypeptide; however, the molecule may include some additional bases or moieties which do not deleteriously affect the basic characteristics of the composition.

By a "recombinant polypeptide" is intended a polypeptide which has been prepared by recombinant DNA techniques as described herein. In general, the gene coding for the desired polypeptide is cloned and then expressed in transformed organisms, as described further below. The host organism expresses the foreign gene to produce the polypeptide under expression conditions. Alternatively, the promoter controlling expression of an endogenous polypeptide can be altered to render a recombinant polypeptide. It is particularly advantageous to produce polypeptides recombinantly as recombinant production generally allows for higher yields from less starting material, and renders a far purer product. Thus, the polypeptides of the invention can be produced in the absence of other molecules normally present in cells. For example, human polypeptide compositions free of any trace of human protein contaminants can be readily obtained because the only human protein produced by a recombinant non-human host cell is the recombinant human polypeptide. Potential viral agents from natural sources and viral components pathogenic to humans are also avoided.

The term "polynucleotide" or "nucleic acid molecule" as used herein refers to a polymeric form of nucleotides of any length, either ribonucleotides or deoxyribonucleotides. This term refers only to the primary structure of the molecule and thus includes double- and single-stranded DNA and RNA. It also includes known types of modifications, for example, labels which are known in the art, methylation, "caps", substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example proteins (including for e.g., nucleases, toxins, antibodies, signal peptides, poly-L-lysine, etc.), those with intercalators (e.g., acridine, psoralen, etc.), those containing chelates (e.g., metals, radioactive metals, boron, oxidative metals, etc.), those containing alkylators, those with modified linkages (e.g., alpha anomeric nucleic acids, etc.), as well as unmodified forms of the polynucleotide.

The terms "recombinant DNA molecule," or "recombinant polynucleotide" are used herein to refer to a polynucleotide of genomic, cDNA, semisynthetic, or synthetic origin which, by virtue of its origin or manipulation: (1) is not associated with all or a portion of a polynucleotide with which it is associated in nature, (2) is linked to a polynucleotide other than that to which it is linked in nature, or (3) does not occur in nature. Thus, the term encompasses "synthetically derived" nucleic acid molecules.

A "coding sequence" is a nucleic acid molecule which is translated into a polypeptide, usually via mRNA, when placed under the control of appropriate regulatory sequences. The boundaries of the coding sequence may be determined by a translation start codon at the 5'-terminus and a translation stop codon at the 3'-terminus. A coding sequence can include, but is not limited to, cDNA, and recombinant nucleotide sequences.

"Control sequences" refer to nucleic acid sequences which are necessary to effect the expression of coding sequences to which they are ligated. The nature of such control sequences differs depending upon the host organism; in prokaryotes, such control sequences generally include promoter, ribosomal binding site, and transcription termination sequence; in eukaryotes, generally, such control sequences include promoters and transcription termination sequences. The term "control sequences" is intended to include, at a minimum, all components necessary for expression of a coding sequence, and may also include additional components, for example, leader sequences and fusion partner sequences.

A control element, such as a promoter, "directs the transcription" of a coding sequence in a cell when RNA polymerase will bind the promoter and transcribe the coding sequence into mRNA, which is then translated into the polypeptide encoded by the coding sequence.

"Operably linked" refers to a juxtaposition wherein the components so described are in a relationship permitting them to function in their intended manner. A control sequence "operably linked" to a coding sequence is ligated in such a way that expression of the coding sequence is achieved under conditions compatible with the control sequences. The control elements need not be contiguous with the coding sequence, so long as they function to direct the expression thereof. Thus, for example, intervening untranslated yet transcribed sequences can be present between a promoter and the coding sequence and the promoter can still be considered "operably linked" to the coding sequence.

As used herein, the term "expression cassette" refers to a molecule comprising at least one coding sequence operably linked to a control sequence which includes all nucleotide sequences required for the transcription of cloned copies of the coding sequence and the translation of the mRNAs in an appropriate host cell. Such expression cassettes can be used to express eukaryotic genes in a variety of hosts such as bacteria, blue-green algae, plant cells, yeast cells, insect cells and animal cells. Under the invention, expression cassettes can include, but are not limited to, cloning vectors, specifically designed plasmids, viruses or virus particles. The cassettes may further include an origin of replication for autonomous replication in host cells, selectable markers, various restriction sites, a potential for high copy number and strong promoters.

By "vector" is meant any genetic element, such as a plasmid, phage, transposon, cosmid, chromosome, virus etc., which is capable of replication when associated with the proper control elements and which can transfer gene sequences between cells. Thus, the term includes cloning and expression vehicles, as well as viral vectors.

A cell has been "transformed" by an exogenous polynucleotide when the polynucleotide has been introduced inside the cell membrane. The exogenous polynucleotide may or may not be integrated (covalently linked) into chromosomal DNA making up the genome of the cell. In procaryotes and yeasts, for example, the exogenous DNA may be maintained on an episomal element, such as a plasmid. With respect to eucaryotic cells, a stably transformed cell is one in which the exogenous DNA has become integrated into the chromosome so that it is inherited by daughter cells through chromosome replication. This stability is demonstrated by the ability of the eucaryotic cell to establish cell lines or clones comprised of a population of daughter cells containing the exogenous DNA.

A "host cell" is a cell which has been transformed, or is capable of transformation, by an exogenous nucleic acid molecule.

"Homology" refers to the percent similarity between two polynucleotide or two polypeptide moieties. Two DNA, or two polypeptide sequences are "substantially homologous" to each other when the sequences exhibit at least about 50%, preferably at least about 70% to 75%, more preferably at least about 80%-85%, preferably at least about 90%, and most preferably at least about 95%-98% sequence homology, or any percent homology between the specified ranges, over a defined length of the molecules. As used herein, substantially homologous also refers to sequences showing complete identity to the specified DNA or polypeptide sequence.

In general, "identity" refers to an exact nucleotide-to-nucleotide or amino acid-to-amino acid correspondence of two polynucleotides or polypeptide sequences, respectively. Percent identity can be determined by a direct comparison of the sequence information between two molecules by aligning the sequences, counting the exact number of matches between the two aligned sequences, dividing by the length of the shorter sequence, and multiplying the result by 100.

Preferably, naturally or non-naturally occurring protein variants have amino acid sequences which are at least 70%, 80%, 85%, 90% or 95% or more homologous to the particular KGF fragment derived from FIG. 1. More preferably, the molecules are 98% or 99% homologous. Percent homology is determined using the Smith-Waterman homology search algorithm using an affine gap search with a gap open penalty of 12 and a gap extension penalty of 2, BLOSUM matrix of 62. The Smith-Waterman homology search algorithm is taught in Smith and Waterman, *Adv. Appl. Math.* 2:482-489 (1981).

Alternatively, homology can be determined by hybridization of polynucleotides under conditions which form stable duplexes between homologous regions, followed by digestion with single-stranded-specific nuclease(s), and size determination of the digested fragments. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; *DNA Cloning*, supra; *Nucleic Acid Hybridization*, supra.

The terms "effective amount" or "pharmaceutically effective amount" refer to a nontoxic but sufficient amount of the agent to provide the desired biological result. That result can be reduction and/or alleviation of the signs, symptoms, or causes of a disease, or any other desired alteration of a biological system. For example, an effective amount of a KGF fragment for use with the present methods is an amount sufficient to stimulate epithelial cell stimulation or proliferation, and preferably an amount sufficient to cause increased healing of wounds and/or burns, and other disorders where epithelial cell proliferation is desired. Such amounts are described below. An appropriate "effective" amount in any individual case may be determined by one of ordinary skill in the art using routine experimentation.

By "pharmaceutically acceptable" or "pharmacologically acceptable" is meant a material which is not biologically or otherwise undesirable, i.e., the material may be administered to an individual without causing any undesirable biological effects or interacting in a deleterious manner with any of the components of the composition in which it is contained.

By "physiological pH" or a "pH in the physiological range" is meant a pH in the range of approximately 7.0 to 8.0 inclusive. Preferred physiological pH is in the range of approximately 7.2 to 7.6 inclusive.

As used herein, the term "subject" encompasses mammals and non-mammals. Examples of mammals include, but are not limited to, any member of the Mammalia class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. The term does not denote a particular age or gender.

II. MODES OF CARRYING OUT THE INVENTION

Before describing the present invention in detail, it is to be understood that this invention is not limited to particular formulations or process parameters as such may, of course, vary. It is also to be understood that the terminology used herein is for the purpose of describing particular embodiments of the invention only, and is not intended to be limiting.

Although a number of compositions and methods similar or equivalent to those described herein can be used in the practice of the present invention, the preferred materials and methods are described herein.

The present invention is based on the discovery that certain KGF polypeptide fragments and analogs of these fragments, which retain only a portion of the full-length sequence, show enhanced bioactivity relative to the full-length sequence. Thus, smaller amounts of the polypeptide may be used in compositions than would be necessary with the full-length molecule. In certain instances, there is less occurrence of non-specific side-effects when compositions including the molecules described herein are administered.

The present invention particularly relates to compositions comprising KGF fragments which exhibit an increase in bioactivity relative to $KGF_{163}$ as determined by the Balb/MK bioactivity assay specified herein and which specifically stimulate epithelial cell proliferation. Particularly, activity of the KGF fragments and analogs is measured by determining the $ED_{50}$ value using Balb/Mk cells, said value defined by the concentration of KGF fragment that causes half maximal stimulation of cell proliferation. The cells are cultured for 7 days, as described below in the examples. The bioactivity of the KGF fragments herein is preferably at least about 1.2 to 1.5-fold, preferably, about 2-fold and, more preferably, about 2- to 10-fold greater or more than that of the full-length KGF protein, when compared in the cell proliferation assay, and may be as much as 10- to 100-fold greater or more than full-length KGF, as determined using stimulation of DNA synthesis in Balb/Mk cells maintained in a chemically defined medium, as described herein and in PCT Patent Application, No. WO 90/08771. Due to the enhanced activity level, the polypeptides of the subject invention allow the use of 90% or less, such as 5%-90%, or 10%-50%, or any number therebetween, on a per molecule basis (i.e., adjusted for the molecular weight) of the amount of $KGF_{163}$ that would be necessary in corresponding compositions to achieve the same biological results.

Particular polypeptides for use herein include but are not limited to the following:

$KGF_{des1-15}$ consisting of the contiguous amino acid sequence depicted at amino acid residues 16-163, inclusive, of FIG. 1; an analog of $KGF_{des1-15}$ consisting of the contiguous amino acid sequence depicted at amino acid residues 16-163, inclusive, of FIG. 1 and having an additional N-terminal methionine;

$KGF_{des1-18}$ consisting of the contiguous amino acid sequence depicted at amino acid residues 19-163, inclusive, of FIG. 1; an analog of $KGF_{des1-18}$ consisting of the contiguous amino acid sequence depicted at amino acid residues 19-163, inclusive, of FIG. 1 and having an additional N-terminal methionine;

$KGF_{des1-19}$ consisting of the contiguous amino acid sequence depicted at amino acid residues 20-163, inclusive, of FIG. 1; an analog $KGF_{des1-19}$ consisting of the contiguous amino acid sequence depicted at amino acid residues 20-163, inclusive, of FIG. 1 with an additional N-terminal methionine;

$KGF_{des1-20}$ consisting of the contiguous amino acid sequence depicted at amino acid residues 21-163, inclusive, of FIG. 1; an analog of $KGF_{des1-20}$ consisting of the contiguous amino acid sequence depicted at amino acid residues 21-163, inclusive, of FIG. 1 with an additional N-terminal methionine;

$KGF_{des1-21}$ consisting of the contiguous amino acid sequence depicted at amino acid residues 22-163, inclusive, of FIG. 1; an analog of $KGF_{des1-21}$ consisting of the contiguous amino acid sequence depicted at amino acid residues 22-163, inclusive, of FIG. 1 with an additional N-terminal methionine;

KGF$_{des1-22}$ consisting of the contiguous amino acid sequence depicted at amino acid residues 23-163, inclusive, of FIG. 1; an analog of KGF$_{des1-22}$ consisting of the contiguous amino acid sequence depicted at amino acid residues 23-163, inclusive, of FIG. 1 with an additional N-terminal methionine; an analog of KGF$_{des1-22}$ consisting of the contiguous amino acid sequence depicted at amino acid residues 23-163, inclusive, of FIG. 1 with the N-terminal arginine residue substituted with an alanine residue;

KGF$_{des1-24}$ consisting of the contiguous amino acid sequence depicted at amino acid residues 25-163, inclusive, of FIG. 1; an analog of KGF$_{des1-24}$ consisting of the contiguous amino acid sequence depicted at amino acid residues 25-163, inclusive, of FIG. 1 with an additional N-terminal methionine; and KGF$_{des1-25}$ consisting of the contiguous amino acid sequence depicted at amino acid residues 26-163, inclusive, of FIG. 1; and an analog of KGF$_{des1-25}$ consisting of the contiguous amino acid sequence depicted at amino acid residues 26-163, inclusive, of FIG. 1 with an additional N-terminal methionine.

Also contemplated for use in the subject compositions are biologically active analogs of the above-specified fragments, wherein the biologically active analogs consist of the same number of amino acids as the above fragments and have at least about 50%, preferably at least about 70%, preferably at least about 75%, preferably at least about 80%, preferably at least about 85%, preferably at least about 90%, preferably at least about 95%, and preferably at least about 98% sequence homology thereto, as determined as described above. For example, the biologically active analog may be an analog of KGF$_{des-15}$ that consists of 148 amino acids and has at least 70% sequence homology thereto; an analog of KGF$_{des-18}$ that consists of 145 amino acids and has at least 70% sequence homology thereto; an analog of KGF$_{des-19}$ that consists of 144 amino acids and has at least 70% sequence homology thereto; an analog of KGF$_{des-20}$ that consists of 143 amino acids and has at least 70% sequence homology thereto; an analog of KGF$_{des-21}$ that consists of 142 amino acids and has at least 70% sequence homology thereto; an analog of KGF$_{des-22}$ that consists of 141 amino acids and has at least 70% sequence homology thereto; an analog of KGF$_{des-24}$ that consists of 139 amino acids and has at least 70% sequence homology thereto; and an analog of KGF$_{des-25}$ that consists of 138 amino acids and has at least 70% sequence homology thereto.

The amount of KGF polypeptide for use in the subject compositions relative to KGF$_{163}$ will vary depending on the particular fragment of interest. In general, compositions will comprise about 90%, or less, even 75%, or less, 50%, or less, 35%, or less, 25%, or less, or 10% or less, on a per molecule basis (i.e., adjusted for molecular weight), of the amount of KGF$_{163}$ in a corresponding composition that would be necessary to achieve the desired result, such as to promote epithelial cell division and/or proliferation. Thus, for example, the compositions described herein may include 5%-90%, or 10%-90%, or 10%-75%, or 10%-50%, or 10%-25%, or 10%-20% on a per molecule basis, of the amount of KGF$_{163}$ in a corresponding composition that would be necessary to achieve the desired result. It is to be understood that particular percentages between these ranges are also contemplated herein.

Particularly, if the KGF fragment is KGF$_{des1-15}$, KGF$_{des1-18}$, KGF$_{des1-19}$, KGF$_{des1-20}$, KGF$_{des1-21}$, KGF$_{des1-22}$, KGF$_{des1-24}$, KGF$_{des1-25}$, or polypeptides derived from these molecules, the amount may be 75%, or less, such as 10% to 75%. If the KGF fragment is KGF$_{des1-22}$ or KGF$_{des1-24}$, or polypeptides derived from these molecules, the amount used may 50%, or less, or even 25%, or 20%, or less, such as 5% to 50%. For KGF$_{des1-24}$ and polypeptides derived therefrom, for example, the amount may be 10%, or less, such as 2% to 10% of the amount required of KGF$_{163}$ to achieve an equivalent therapeutic response. Appropriate amounts are discussed in detail below.

In a preferred embodiment of the present invention, the KGF fragments of the present invention are produced by recombinant technology, particularly in the case of large-scale commercial production. Recombinant DNA molecules and expression vectors encoding the polypeptides of the present invention can be made and the genes expressed by conventional gene expression technology using methods well-known in the art, as discussed in more detail below. Analogs of particular KGF fragments may also be made recombinantly, for example, by site-directed mutagenesis. Thus, all references to embodiments of the present invention as they relate to particular KGF fragments apply equally to analogs of the fragments.

In one embodiment of the present invention, the KGF fragment can be made by isolating native, mature KGF from cells producing the same, such as M426 human embryonic fibroblasts (Aaronson, S. A. and Todaro, G. J. *Virology* (1968) 36:254-261), using techniques described in, e.g., U.S. Pat. No. 5,731,170. N-terminal amino acid residues can then be deleted from the recovered molecule. Such deletion can be performed by any conventional techniques known in the art.

Alternatively, polypeptides for use in the subject compositions can be synthesized chemically, by any of several techniques that are known to those skilled in the peptide art. See, e.g., J. M. Stewart and J. D. Young, *Solid Phase Peptide Synthesis* (Pierce Chemical Co., Rockford, Ill. 1984) and G. Barany and R. B. Merrifield, *The Peptides: Analysis, Synthesis, Biology*, editors E. Gross and J. Meienhofer, Vol. 2, (Academic Press, New York, 1980), pp. 3-254, for solid phase peptide synthesis techniques; and M. Bodansky, *Principles of Peptide Synthesis*, (Springer-Verlag, Berlin 1984) and E. Gross and J. Meienhofer, Eds., *The Peptides: Analysis, Synthesis, Biology*, Vol. 1, for classical solution synthesis. The polypeptides of the present invention can also be chemically prepared by the method of simultaneous multiple peptide synthesis. See, e.g., Houghten *Proc. Natl. Acad. Sci. USA* (1985) 82:5131-5135; U.S. Pat. No. 4,631,211.

In an alternative embodiment, the KGF fragments can be made by isolating the coding sequence of native KGF$_{163}$, deleting the codons that encode the amino acid residues to be deleted, inserting the modified coding sequence into an expression vector, transforming host cells with the expression vector to produce the recombinant KGF fragments and analogs, and isolating the recombinant KGF fragment using conventional purification techniques.

In a further embodiment of the present invention, the coding sequence of the KGF fragment can be obtained by conventional techniques, including the isolation of the coding sequence of KGF$_{163}$ from a cDNA library known to contain such, and deleting therefrom the sequence encoding the portion of amino acid residues to be deleted. Deletion of the coding sequence of the N-terminal amino acids can be accomplished in vivo or in vitro. The former can be achieved, for example, by expression of the KGF$_{163}$ coding sequence in an appropriate expression system. The latter can be achieved by known PCR techniques using primers that exclude the N-terminal sequences.

Preferably, polypeptides for use in the present compositions are produced recombinantly, by expression of a polynucleotide encoding the same. Methods for the recombinant production of KGF fragments are well known. See, e.g., U.S. Pat. Nos. 5,677,278, 5,773,586, 5,843,883, 5,863,767 and 6,074,848, all to Gospodarowicz et al.; International Publications WO 96/11951 and WO 96/11949; and Osslund et al. *Protein Sci.* (1998) 7:1681-1690.

In particular, the molecules for use with the present invention can be made using standard techniques of molecular biology. For example, polynucleotide sequences coding for the above-described molecules can be obtained using recombinant methods, such as by screening cDNA and genomic libraries from cells expressing the gene, or by deriving the gene from a vector known to include the same. Furthermore, the desired gene can be isolated directly from cells and tissues containing the same, using standard techniques, such as phenol extraction and PCR of cDNA or genomic DNA. See, e.g., Sambrook et al., supra, for a description of techniques used to obtain and isolate DNA. The gene of interest can also be produced synthetically, rather than cloned. The molecules can be designed with appropriate codons for the particular sequence. The complete sequence is then assembled from overlapping oligonucleotides prepared by standard methods and assembled into a complete coding sequence. See, e.g., Edge (1981) *Nature* 292:756; Nambair et al. (1984) *Science* 223:1299; and Jay et al. (1984) *J. Biol. Chem.* 259:6311.

Thus, particular nucleotide sequences can be obtained from vectors harboring the desired sequences or synthesized completely or in part using various oligonucleotide synthesis techniques known in the art, such as site-directed mutagenesis and polymerase chain reaction (PCR) techniques where appropriate. See, e.g., Sambrook, supra. In particular, one method of obtaining nucleotide sequences encoding the desired sequences is by annealing complementary sets of overlapping synthetic oligonucleotides produced in a conventional, automated polynucleotide synthesizer, followed by ligation with an appropriate DNA ligase and amplification of the ligated nucleotide sequence via PCR. See, e.g., Jayaraman et al. (1991) *Proc. Natl. Acad. Sci. USA* 88:4084-4088. Additionally, oligonucleotide directed synthesis (Jones et al. (1986) *Nature* 54:75-82), oligonucleotide directed mutagenesis of pre-existing nucleotide regions (Riechmann et al. (1988) *Nature* 332:323-327 and Verhoeyen et al. (1988) *Science* 239:1534-1536), and enzymatic filling-in of gapped oligonucleotides using $T_4$ DNA polymerase (Queen et al. (1989) *Proc. Natl. Acad. Sci. USA* 86:10029-10033) can be used under the invention to provide molecules having altered or enhanced receptor-binding capabilities, and/or reduced immunogenicity.

Once coding sequences have been prepared or isolated, such sequences can be cloned into any suitable vector or replicon. Numerous cloning vectors are known to those of skill in the art, and the selection of an appropriate cloning vector is a matter of choice. Suitable vectors include, but are not limited to, plasmids, phages, transposons, cosmids, chromosomes or viruses which are capable of replication when associated with the proper control elements.

The coding sequence is then placed under the control of suitable control elements, depending on the system to be used for expression. Thus, the coding sequence can be placed under the control of a promoter, ribosome binding site (for bacterial expression) and, optionally, an operator, so that the DNA sequence of interest is transcribed into RNA by a suitable transformant. The coding sequence may or may not contain a sequence coding for a signal peptide or leader sequence which can later be removed by the host in post-translational processing. See, e.g., U.S. Pat. Nos. 4,431,739; 4,425,437; 4,338,397. If a signal sequence is present, it can either be the native sequence or it may be a heterologous signal sequence.

In addition to control sequences, it may be desirable to add regulatory sequences which allow for regulation of the expression of the sequences relative to the growth of the host cell. Regulatory sequences are known to those of skill in the art, and examples include those which cause the expression of a gene to be turned on or off in response to a chemical or physical stimulus, including the presence of a regulatory compound. Other types of regulatory elements may also be present in the vector. For example, enhancer elements may be used herein to increase expression levels of the constructs. Examples include the SV40 early gene enhancer (Dijkema et al. (1985) *EMBO J.* 4:761), the enhancer/promoter derived from the long terminal repeat (LTR) of the Rous Sarcoma Virus (Gorman et al. (1982) *Proc. Natl. Acad. Sci. USA* 79:6777) and elements derived from human CMV (Boshart et al. (1985) *Cell* 41:521), such as elements included in the CMV intron A sequence (U.S. Pat. No. 5,688,688). The expression cassette may further include an origin of replication for autonomous replication in a suitable host cell, one or more selectable markers, one or more restriction sites, a potential for high copy number and a strong promoter.

An expression vector is constructed so that the particular coding sequence is located in the vector with the appropriate regulatory sequences, the positioning and orientation of the coding sequence with respect to the control sequences being such that the coding sequence is transcribed under the "control" of the control sequences (i.e., RNA polymerase which binds to the DNA molecule at the control sequences transcribes the coding sequence). Modification of the sequences encoding the molecule of interest may be desirable to achieve this end. For example, in some cases it may be necessary to modify the sequence so that it can be attached to the control sequences in the appropriate orientation; i.e., to maintain the reading frame. The control sequences and other regulatory sequences may be ligated to the coding sequence prior to insertion into a vector. Alternatively, the coding sequence can be cloned directly into an expression vector which already contains the control sequences and an appropriate restriction site.

As explained above, it may also be desirable to produce mutants or analogs of the reference KGF fragment. Mutants or analogs may be prepared by the deletion of a portion of the sequence encoding the KGF fragment, by insertion of a sequence, and/or by substitution of one or more nucleotides within the sequence. Techniques for modifying nucleotide sequences, such as site-directed mutagenesis, and the like, are well known to those skilled in the art. See, e.g., Sambrook et al., supra; Kunkel, T. A. (1985) *Proc. Natl. Acad. Sci. USA* (1985) 82:448; Geisselsoder et al. (1987) *BioTechniques* 5:786; Zoller and Smith (1983) *Methods Enzymol.* 100:468; Dalbie-McFarland et al. (1982) *Proc. Natl. Acad. Sci USA* 79:6409.

The molecules can be expressed in a wide variety of systems, including insect, mammalian, bacterial, viral and yeast expression systems, all well known in the art. For example, insect cell expression systems, such as baculovirus systems, are known to those of skill in the art and described in, e.g., Summers and Smith, *Texas Agricultural Experiment Station Bulletin No.* 1555 (1987). Materials and methods for baculovirus/insect cell expression systems are commercially available in kit form from, inter alia, Invitrogen, San Diego Calif. ("MaxBac" kit). Similarly, bacterial and mammalian cell expression systems are well known in the art and described in, e.g., Sambrook et al., supra. Yeast expression systems are also known in the art and described in, e.g., *Yeast Genetic Engineering* (Barr et al., eds., 1989) Butterworths, London.

A number of appropriate host cells for use with the above systems are also known. For example, mammalian cell lines are known in the art and include immortalized cell lines available from the American Type Culture Collection (ATCC), such as, but not limited to, Chinese hamster ovary (CHO) cells, HeLa cells, baby hamster kidney (BHK) cells, monkey kidney cells (COS), human embryonic kidney cells, human hepatocellular carcinoma cells (e.g., Hep G2), Madin-Darby bovine kidney ("MDBK") cells, as well as others. Similarly, bacterial hosts such as *E. coli, Bacillus subtilis*, and *Streptococcus* spp., will find use with the present expression constructs. Yeast hosts useful in the present invention include inter alia, *Saccharomyces cerevisiae, Candida albicans, Candida maltosa, Hansenula polymorpha, Kluyveromyces fragilis, Kluyveromyces lactis, Pichia guillerimondii, Pichia pastoris, Schizosaccharomyces pombe* and *Yarrowia lipolytica*. Insect cells for use with baculovirus expression vectors include, inter alia, *Aedes aegypti, Autographa californica, Bombyx mori, Drosophila melanogaster, Spodoptera frugiperda*, and *Trichoplusia ni*.

Intracellular expression of the truncated KGF polypeptides and analogs thereof in yeast is particularly desirable. Such systems avoid problems which may arise with purification from bacteria, such as *E. coli*, including the presence of large amounts of DNA, endotoxins, and protein contaminants. Moreover, naturally occurring yeast enzymes efficiently cleave the N-terminal methionine which may be present when the molecules are recombinantly produced and there is no need to overexpress the enzyme when a yeast system is used. Additionally, although KGF is a naturally secreted protein, when native and truncated KGF, and analogs thereof, are produced internally in yeast without secretion, they are soluble, properly folded and active.

Nucleic acid molecules comprising nucleotide sequences of interest can be stably integrated into a host cell genome or maintained on a stable episomal element in a suitable host cell using various gene delivery techniques well known in the art. See, e.g., U.S. Pat. No. 5,399,346.

Depending on the expression system and host selected, the molecules are produced by growing host cells transformed by an expression vector described above under conditions whereby the protein is expressed. The expressed protein is then isolated from the host cells and purified. If the expression system secretes the protein into growth media, the product can be purified directly from the media. If it is not secreted, it can be isolated from cell lysates. The selection of the appropriate growth conditions and recovery methods are within the skill of the art.

The KGF fragments are then formulated into pharmaceutical compositions, described further below, for delivery to a subject. Alternatively, polynucleotides encoding the polypeptide of interest may be delivered directly to the subject and expressed in vivo. A number of viral based systems have been developed for direct gene transfer into mammalian cells. In this regard, retroviruses provide a convenient platform for gene delivery systems. A selected nucleotide sequence encoding the desired polypeptide can be inserted into a vector and packaged in retroviral particles using techniques known in the art. The recombinant virus can then be isolated and delivered to a subject. A number of suitable retroviral systems have been described (U.S. Pat. No. 5,219,740; Miller and Rosman (1989) *BioTechniques* 7:980-990; Miller, A. D. (1990) *Human Gene Therapy* 1:5-14; Scarpa et al. (1991) *Virology* 180:849-852; Burns et al. (1993) *Proc. Natl. Acad. Sci. USA* 90:8033-8037; and Boris-Lawrie and Temin (1993) *Cur. Opin. Genet. Develop.* 3:102-109.

A number of suitable adenovirus vectors have also been described. Unlike retroviruses which integrate into the host genome, adenoviruses persist extrachromosomally thus minimizing the risks associated with insertional mutagenesis (Haj-Ahmad and Graham (1986) *J. Virol.* 57:267-274; Bett et al. (1993) *J. Virol.* 67:5911-5921; Mittereder et al. (1994) *Human Gene Therapy* 5:717-729; Seth et al. (1994) *J. Virol.* 68:933-940; Barr et al. (1994) *Gene Therapy* 1:51-58; Berkner, K. L. (1988) *BioTechniques* 6:616-629; and Rich et al. (1993) *Human Gene Therapy* 4:461-476). Various adeno-associated virus (AAV) vector systems have been developed recently for gene delivery. Such systems can include control sequences, such as promoter and polyadenylation sites, as well as selectable markers or reporter genes, enhancer sequences, and other control elements which allow for the induction of transcription. AAV vectors can be readily constructed using techniques well known in the art. See, e.g., U.S. Pat. Nos. 5,173,414 and 5,139,941; International Publication Nos. WO 92/01070 (published Jan. 23, 1992) and WO 93/03769 (published Mar. 4, 1993); Lebkowski et al. (1988) *Molec. Cell. Biol.* 8:3988-3996; Vincent et al. (1990) *Vaccines* 90 (Cold Spring Harbor Laboratory Press); Carter, B. J. (1992) *Current Opinion in Biotechnology* 3:533-539; Muzyczka, N. (1992) *Current Topics in Microbiol. and Immunol.* 158:97-129; Kotin, R. M. (1994) *Human Gene Therapy* 5:793-801; Shelling and Smith (1994) *Gene Therapy* 1:165-169; and Zhou et al. (1994) *J. Exp. Med.* 179:1867-1875.

Additional viral vectors which will find use for delivering the nucleic acid molecules encoding the molecules of the present invention by gene transfer include those derived from the pox family of viruses, such as vaccinia virus and avian poxvirus. See, e.g., International Publication Nos. WO 91/12882; WO 89/03429; and WO 92/03545.

Molecular conjugate vectors, such as the adenovirus chimeric vectors described in Michael et al. (1993) *J. Biol. Chem.* 268:6866-6869 and Wagner et al. (1992) *Proc. Natl. Acad. Sci. USA* 89:6099-6103, can also be used for gene delivery under the invention.

Members of the Alphavirus genus, such as but not limited to vectors derived from the Sindbis and Semliki Forest viruses, will also find use as viral vectors for delivering the gene of interest. For a description of Sinbus-virus derived vectors useful for the practice of the instant methods, see, Dubensky et al., *J. Virol.* (1996) 70:508-519; and International Publication Nos. WO 95/07995 and WO 96/17072.

The gene of interest can also be delivered without a viral vector. For example, the gene can be packaged in liposomes prior to delivery to the subject or to cells derived therefrom, with or without the accompanying antigen. Lipid encapsulation is generally accomplished using liposomes which are able to stably bind or entrap and retain nucleic acid. For a review of the use of liposomes as carriers for delivery of nucleic acids, see, Hug and Sleight, *Biochim. Biophys. Acta.* (1991) 1097:1-17; Straubinger et al., in *Methods of Enzymology* (1983), Vol. 101, pp. 512-527.

The KGF fragments of the present invention can be used for identification of receptor recognition sites as well as for the design of peptide agonists or antagonists. Moreover, in view of the unique specificity of KGF for keratinocytes, its inability to induce the proliferation of vascular endothelial cells or fibroblasts, and its lack of cytotoxicity, the truncated molecules and analogs thereof are a preferred agent of choice for wound healing applications, particularly where there is a desire to promote re-epithelialization of the skin. The truncated KGF molecules are also particularly useful in corneal epithelial repair. Other uses of the molecules include applications that utilize the specificity for epithelial cells found in the gastrointestinal tract.

The fragments of the present invention may be conjugated to other molecules suitable for its intended use. For example, the KGF polypeptides can be conjugated to a toxin molecule, such as ricin A, diphtheria toxin, or saporin for destruction of its target cell, i.e., epithelial cells, particularly, keratinocytes. Such KGF toxin conjugates suitable for use herein can be produced by methods known in the art, for example, U.S. Pat. Nos. 4,771,128, 4,808,705, and 4,894,443 and International Publication No. WO 92/04918.

The compositions of the invention comprise the molecules described above, together with one or more pharmaceutically acceptable excipients or vehicles, and optionally other therapeutic and/or prophylactic ingredients. Such excipients include liquids such as water, saline, glycerol, polyethyleneglycol, hyaluronic acid, ethanol, etc. Suitable excipients for nonliquid formulations are also known to those of skill in the art. Pharmaceutically acceptable salts can be used in the compositions of the present invention and include, for example, mineral acid salts such as hydrochlorides, hydrobromides, phosphates, sulfates, and the like; and the salts of organic acids such as acetates, propionates, malonates, benzoates, and the like. A thorough discussion of pharmaceutically acceptable excipients and salts is available in *Remington's Pharmaceutical Sciences*, 18th Edition (Easton, Pa.: Mack Publishing Company, 1990).

Additionally, auxiliary substances, such as wetting or emulsifying agents, biological buffering substances, surfactants, and the like, may be present in such vehicles. A biological buffer can be virtually any solution which is pharmacologically acceptable and which provides the formulation with the desired pH, i.e., a pH in the physiologically acceptable range. Examples of buffer solutions include saline, phosphate buffered saline, Tris buffered saline, Hank's buffered saline, and the like.

Particularly preferred compositions are those which are applied topically, such as ointments, pastes, powders, dressings, creams and plasters. Such topical compositions may also include topical anesthetics, such as but not limited to, benzocaine, lidocaine, dibucaine, dyclonine hydrochloride, pramoxine hydrochloride, proparacaine hydrochloride, tetracaine, benoxinate hydrochloride, butamben picrate, clove oil and eugenol, as well as combinations and derivatives of the above. Ophthalmic compositions for direct delivery for the eye are also of particular use with the KGF fragments of the invention. See, e.g., *Remington's Pharmaceutical Sciences*, 18th Edition (Easton, Pa.: Mack Publishing Company, 1990) for a discussion of various topical and ophthalmic compositions.

As explained above, once formulated, the compositions of the invention are generally administered topically or ophthalmically. However, other modes of administration include parenteral administration, for example, intravenously, intra-arterially, intra-articularly (e.g., into the knee), subcutaneously, intradermally, intramuscularly, transdermally, intranasally, mucosally, and by aerosol administration. For example, the composition can be administered by inhalation, e.g., as a nasal or mouth spray or aerosol. The compositions may also be delivered in situ, e.g., by implantation.

A pharmaceutically or therapeutically effective amount of the composition will be delivered to the subject. The precise effective amount will vary from subject to subject and will depend upon the species, age, the subject's size and health, the nature and extent of the condition being treated, recommendations of the treating physician, and the therapeutics or combination of therapeutics selected for administration. Thus, the effective amount for a given situation can be determined by routine experimentation. For purposes of the present invention, generally a therapeutic amount if administered topically will be in the range of about 0.1 µg/cm$^2$ of wound to approximately 500 µg/cm$^2$ of wound, preferably about 1 µg/cm$^2$ of wound to approximately 100 µg/cm$^2$ of wound, more preferably about 1-10 µg/cm$^2$ of wound to approximately 50 µg/cm$^2$, or any integer between these values, such as 21, 22, 23, 24 . . . 30, 31, 32, 33, 34 . . . 40, 41, 43 . . . 50 . . . 60 . . . , and so on. For parenteral administration, typical doses will be in the range of about 0.01 µg/kg body weight/day to about 100 µg/kg/day, more preferably about 0.1 µg/kg/day to about 80 µg/kg/day, more preferably 1 µg/kg/day to about 40 µg/kg/day in one or more doses. Typically, if polynucleotides are delivered, the doses will be at least an order of magnitude lower. The subject may be administered as many doses as is required to reduce and/or alleviate the signs, symptoms, or causes of the disorder in question, or bring about any other desired alteration of a biological system. In any event, the amount of KGF fragment present in the subject composition is an amount less than the amount of $KGF_{163}$ necessary in order to obtain an equivalent response. This amount is readily determined by comparing the bioactivity of the fragment in question to that of $KGF_{163}$, as described above.

III. EXPERIMENTAL

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

Enzymes were purchased from commercial sources, and used according to the manufacturers' directions. Radionucleotides and nitrocellulose filters were also purchased from commercial sources.

In the cloning of DNA fragments, except where noted, all DNA manipulations were done according to standard procedures. See, Sambrook et al., supra. Restriction enzymes, T$_4$ DNA ligase, DNA polymerase I, Klenow fragment, and other biological reagents were purchased from commercial suppliers and used according to the manufacturers' directions. Double-stranded DNA fragments were separated on agarose gels.

Example 1

Construction of Truncated KGF Yeast Vectors for Intracellular Yeast Expression

This example describes a procedure for construction of yeast expression vectors for intracellular expression of the various truncated KGF molecules for use with the subject invention.

The expression vectors included the particular truncated KGF coding sequence under the control of the ADH2/GAPDH promoter, a hybrid yeast promoter. In particular, for each different truncation, two oligos were used (see below), a top strand and a bottom strand. The oligos were annealed and then placed in a ligation reaction. The ligation reactions included the plasmid pSI3, cut at Nco and Sal sites, a Kpn/Sal fragment, encoding a truncated KGF and one of the annealed oligo pairs. The oligo pairs encoded the amino terminus of the particular truncated KGF protein desired and were designed to link the Nco site of the vector to the Kpn site of the KGF encoding fragment. Plasmid pSI3 is a derivative of pYASI1, which was deposited with the ATCC, Manassas, Va., on Feb. 27, 1985, and assigned ATCC Accession No. 20745. The construction of pYASI1 is described in U.S. Pat. No. 4,751,180, incorporated herein by reference in its entirety.

The various oligos for the completed truncated KGFs were as follows. The "X" in the oligo sequences represents a 5' phosphate group.

$KGF_{des1-15}$:
5' XCATGAGCAGCCCTGAGCGACACACAAGAAGTT (SEQ ID NO:1) ATGATTACATGGAAGGAGGGGATATAAGAGTGAGAA GACTCTTCTGTCGAACACAGTGGTAC 3'

5' XCACTGTGTTCGACAGAAGAGTCTTCTCACTCT (SEQ ID NO:2) TATATCCCCTCCTTCCATGTAATCATAACTTCTTG TGTGTCGCTCAGGGCTGCT 3'

$KGF_{des1-18}$:
5' XCATGGAGCGACACACAAGAAGTTATGATTACA (SEQ ID NO:3) TGGAAGGAGGGGATATAAGAGTGAGAAGACTCTTC TGTCGAACACAGTGGTAC 3'

5' XCACTGTGTTCGACAGAAGAGTCTTCTCACTCT (SEQ ID NO:4) TATATCCCCTCCTTCCATGTAATCATAACTTCTTG TGTGTCGCTC 3'

$KGF_{des1-19}$:
5' XCATGCGACACACAAGAAGTTATGATTACATGG (SEQ ID NO:5) AAGGAGGGGATATAAGAGTGAGAAGACTCTTCTGT CGAACACAGTGGTAC 3'

5' XCACTGTGTTCGACAGAAGAGTCTTCTCACTCT (SEQ ID NO:6) TATATCCCCTCCTTCCATGTAATCATAACTTCTTG TGTGTCG 3'

$KGF_{des1-20}$:
5' XCATGCACACAAGAAGTTATGATTACATGGAAG (SEQ ID NO:7) GAGGGGATATAAGAGTGAGAAGACTCTTCTGTCGA ACACAGTGGTAC 3'

5' XCACTGTGTTCGACAGAAGAGTCTTCTCACTCT (SEQ ID NO:8) TATATCCCCTCCTTCCATGTAATCATAACTTCTTG TGTG 3'

$KGF_{des1-21}$:
5' XCATGACCAGAAGTTATGATTACATGGAAGGAG (SEQ ID NO:9) GGGATATAAGAGTGAGAAGACTCTTCTGTCGAACA CAGTGGTAC 3'

5' XCACTGTGTTCGACAGAAGAGTCTTCTCACTCT (SEQ ID NO:10) TATATCCCCTCCTTCCATGTAATCATACTTCTGGT 3'

$KGF_{des1-22}$:
5' XCATGAGAAGTTATGATTACATGGAAGGAGGGG (SEQ ID NO:11) ATATAAGAGTGAGAAGACTCTTCTGTCGAACACAG TGGTAC 3'

5' XCACTGTGTTCGACAGAAGAGTCTTCTCACTCT (SEQ ID NO:12) TATATCCCCTCCTTCCATGTAATCATAACTTCT 3'

$KGF_{des1-24}$:
5' XCATGTATGATTACATGGAAGGAGGGGATATAA (SEQ ID NO:13) GAGTGAGAAGACTCTTCTGTCGAACACAGTGGTAC 3'

5' XCACTGTGTTCGACAGAAGAGTCTTCTCACTCT (SEQ ID NO:14) TATATCCCCTCCTTCCATGTAATCATA 3'

$KGF_{des1-25}$:
5' XCATGGATTACATGGAAGGAGGGGATATAAGAG (SEQ ID NO:15) TGAGAAGACTCTTCTGTCGAACACAGTGGTAC 3'

5' XCACTGTGTTCGACAGAAGAGTCTTCTCACTCT (SEQ ID NO:16) TATATCCCCTCCTTCCATGTAATC 3'

$KGF_{des1-26}$:
5' XCATGTACATGGAAGGAGGGGATATAAGAGTGA (SEQ ID NO:17) GAAGACTCTTCTGTCGAACACAGTGGTAC 3'

5' XCACTGTGTTCGACAGAAGAGTCTTCTCACTCT (SEQ ID NO:18) TATATCCCCTCCTTCCATGTA 3'

$KGF_{des1-30}$:
5' XCATGGGGGATATAAGAGTGAGAAGACTCTTCT (SEQ ID NO:19) GTCGAACACAGTGGTAC 3'

5' XCACTGTGTTCGACAGAAGAGTCTTCTCACTCT (SEQ ID NO:20) TATATCCCC 3'

$KGF_{des1-35}$:
5' XCATGAGAAGACTCTTCTGTCGAACACAGTGGT (SEQ ID NO:21) AC 3'

5' XCACTGTGTTCGACAGAAGAGTCTTCT 3'    (SEQ ID NO:22)

$KGF_{des1-37}$:
5' XCATGCTCTTCTGTCGAACACAGTGGTAC 3'  (SEQ ID NO:23)

5' XCACTGTGTTCGACAGAAGAG 3'  (SEQ ID NO:24)

Additionally, expression vectors encoding mature, full-length KGF ($KGF_{163}$) and a truncated KGF molecule with a deletion of the first 23 N-terminal amino acids, $KGF_{des1-23}$, were produced. See, e.g., U.S. Pat. No. 5,677,278, incorporated herein by reference in its entirety. An analog of $KGF_{des1-22}$, with an alanine residue at the N-terminus instead of the naturally occurring arginine, was also produced.

Example 2

Intracellular Expression of Truncated KGF Molecules by Yeast Cells

The expression vectors described above were used to transform *Saccharomyces cerevisae* cells by lithium acetate transfection, using standard methods. See, e.g., "Guide to Yeast Genetics & Molecular Biology," Methods in Enzymology, Vol. 194 (Academic Press, 1991). Transformants were selected on uracil-deficient media having 2% glucose. Transformants were incubated overnight in 5 ml of leucine-deficient media with 5% glucose at 30° C. in a shaking apparatus. The culture for production of the recombinant truncated molecules was a 20 ml culture, seeded with the overnight culture in YEP medium with 2% glucose for approximately 72 hours.

Example 3

Purification of the Truncated Recombinant KGF Molecules

The cultures from above were centrifuged to form a yeast cell paste and cells were lysed in 10 mM $MgCl_2$, 50 mM Tris, pH 8.0, 0.1 M dithiothrietol (DTT), using standard techniques. The cell lysate was generated as a batch, using glass beads in a Dynomill DKL-Pilot. Lysate generation was complete when cell breakage was ≧95%. The homogenate was cooled to 4-8° C. by using a suitable heat exchanger.

Debris was then removed by centrifugating the lysate at 15,000 g for thirty minutes at 4° C. The NaCl concentration of the supernatant was adjusted to 0.5 M NaCl and recombinant, truncated KGF was purified from the supernatant as follows.

A. Heparin Sepharose™ Affinity Chromatography

Supernatant obtained as described above was immediately applied to a Heparin Sepharose (HS) resin column. The lysed product was allowed to run for approximately 30 minutes at 4° C. through a 30 ml bed of HS resin. The column was equilibrated in a buffer containing 0.5 M NaCl, 0.1 M DTT and 10 mM Tris-HCl at pH 7.3. Once the cell lysate was loaded, the column was washed extensively with the equilibration buffer until the absorbance at 280 nm returned to baseline. Protein was eluted from the HS column with an increasing step-wise NaCl gradient. The NaCl concentrations were 1 M and 2 M NaCl, in 10 mM Tris-HCl at pH 7.3, 0.1 M DTT. The flow rate of the column during elution was approximately 90 ml/hr and 4 ml size fractions were collected.

The fractions were tested for KGF bioactivity utilizing Balb/Mk cells. The assay is described below. The fractions with the highest bioactivity were eluted with 1 M NaCl and were pooled. Before the pooled fractions were loaded onto the next column, the fractions were dialyzed overnight against 0.2 M NaCl, 10 mM Tris-HCl at pH 7.3.

B. Mono S Cation Exchange Chromatography

The pooled fractions eluted from the HS column were loaded with a Super loop onto a Mono S column linked to a fast high pressure liquid chromatography (FPLC) system (Pharmacia, Piscataway, N.J.). The Mono S cation exchange column was equilibrated with 10 mM Tris at pH 7.3. When the pooled fractions were loaded, the column was washed extensively at a flow rate of 1 ml/min. with the equilibration buffer until the absorbance returned to baseline. Then, protein was eluted from the column with a linear NaCl gradient, 0.2 M to 1 M NaCl in 10 mM Tris, at pH 7.3 at a flow rate of 1 ml/min., and 1 ml fractions were collected.

A major protein peak eluted at about 0.6 M NaCl. Fractions across the protein peak were assayed for bioactivity and active fractions were pooled and subjected to SDS-PAGE analysis. The protein concentration of the pooled fractions was determined by Bradford assay according to instructions accompanying the protein assay kit from Bio-Rad (Richmond, Calif., USA).

Example 4

KGF Bioactivity Assay Utilizing Balb/Mk Cells

KGF bioactivity was assessed by the ability of the pooled 0.6 M NaCl fractions to promote growth of Balb/Mk cells. In particular, stock cultures of Balb/Mk cells were grown and maintained in low calcium Dulbecco's modified Eagle medium (DMEM) supplemented with 10% fetal bovine serum, 0.25 µg/ml fungizone, and 10 ng/ml acidic FGF (aFGF). The cells were incubated at 37° C. in a 10% $CO_2$ atmosphere with 99% humidity. For the bioactivity assay, the cells were seeded in 12-well plates at a density of $5 \times 10^3$ cells per well in 1 ml of medium as described above for the stock cultures (except that the seeding medium contained no aFGF), and as described in Gospodarowicz et al. *J. Cell. Physiol.* (1990) 142: 325-333.

Ten microliter aliquots of the desired column fractions were diluted into 1 ml of 0.2% (w/v) gelatin in phosphate buffered saline (PBS). Ten microliters of this dilution were added to Balb/Mk cells seeded in 12-well cluster plates containing 22 mm wells, at $5 \times 10^3$ cells per well, and a 10 µl aliquot of either the diluted column fractions or medium containing 10 ng aFGF were added to the cells every other day.

After seven days in culture, the cells were trypsinized and the final cell density was determined using a Coulter™ counter (Coulter Electronics, Hialeah, Fla., USA). The cells were released from the plates by replacing the culture medium with a solution containing 0.9% NaCl, 0.01 M sodium phosphate (pH 7.4), 0.25% trypsin, and 0.02% EDTA (STV). The cells were incubated in this solution for 5-10 minutes at 37° C. and then the stock culture medium was added to the cells. The cells were then counted using a Coulter™ counter. The final cell density was graphed as a function of column fraction protein concentration. The protein concentration was graphed on a log scale.

The $ED_{50}$ was calculated by (a), dividing in half the difference between the lowest and highest cell density value of the curve; and (b), determining from the graph what protein concentration corresponds to that cell density number obtained in (a).

Figure 2B:
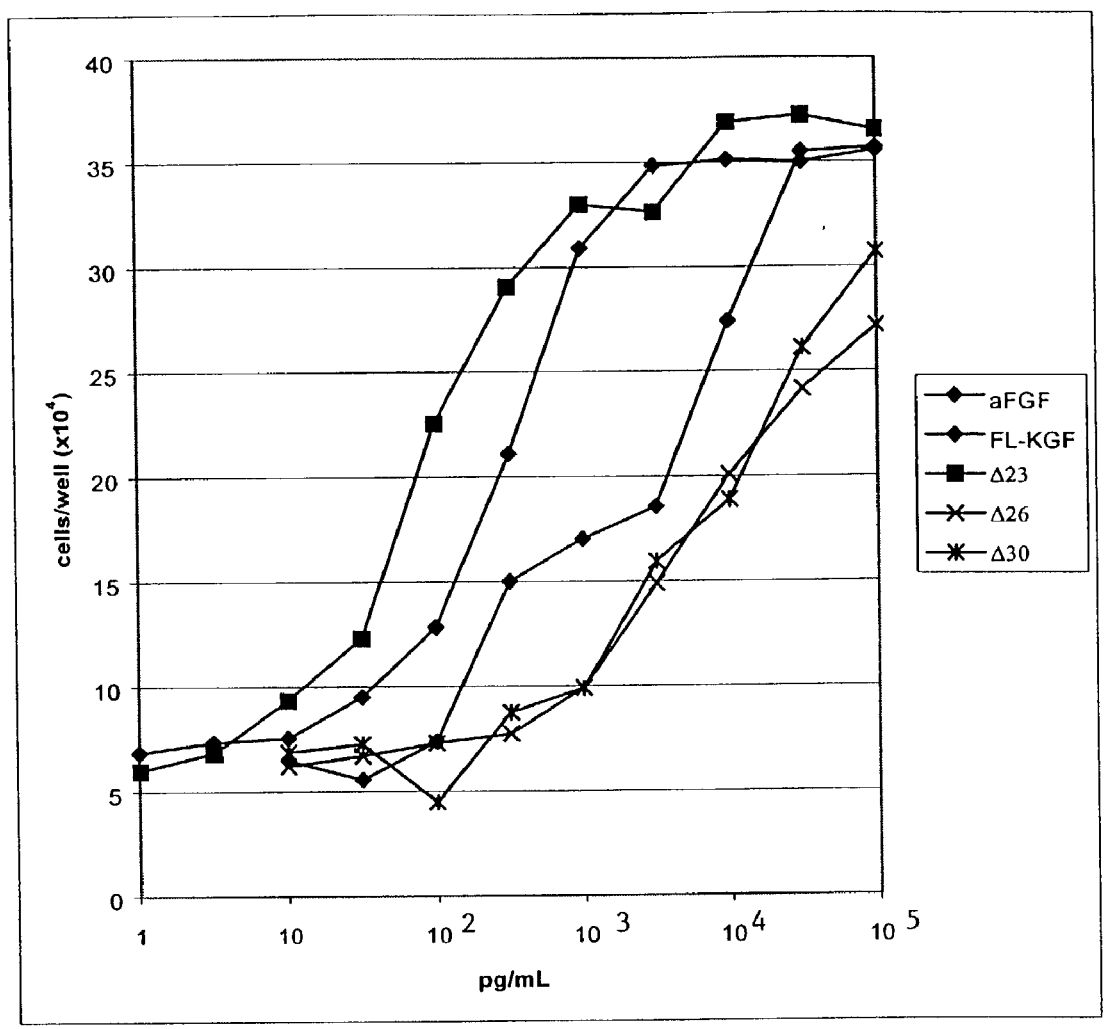

Results of a typical bioassay for $KGF_{des1-22}$, $KGF_{des1-23}$, $KGF_{des1-24}$, $KGF_{des1-26}$ and $KGF_{des1-30}$ are shown in FIG. 2A. A similar comparison was done with $KGF_{des1-23}$, $KGF_{des1-26}$, $KGF_{des1-30}$, acidic FGF (aFGF) and full-length KGF (FL-KGF) and results are shown in FIG. 2B. When the $ED_{50}$ of the different truncated forms was normalized to that of native KGF taken as 100% (Table 1) $KGF_{des1-22}$, $KGF_{des1-23}$ and $KGF_{des1-24}$ had significant increases in their biological activity. In particular, $KGF_{des1-22}$ was approximately 6-fold more active, while $KGF_{des1-23}$ and $KGF_{des1-24}$ were 10-fold more active than native $KGF_{163}$. Even when compared on a per molecule basis and adjusted for molecular weight, these species displayed greatly enhanced activity relative to $KGF_{163}$. Deletion beyond $KGF_{des1-24}$ to $KGF_{des1-26}$ rendered the truncated forms of KGF with comparable activity to the native form, and deletions beyond $KGF_{des1-26}$ led to a reduction in biological activity.

Figure 3:
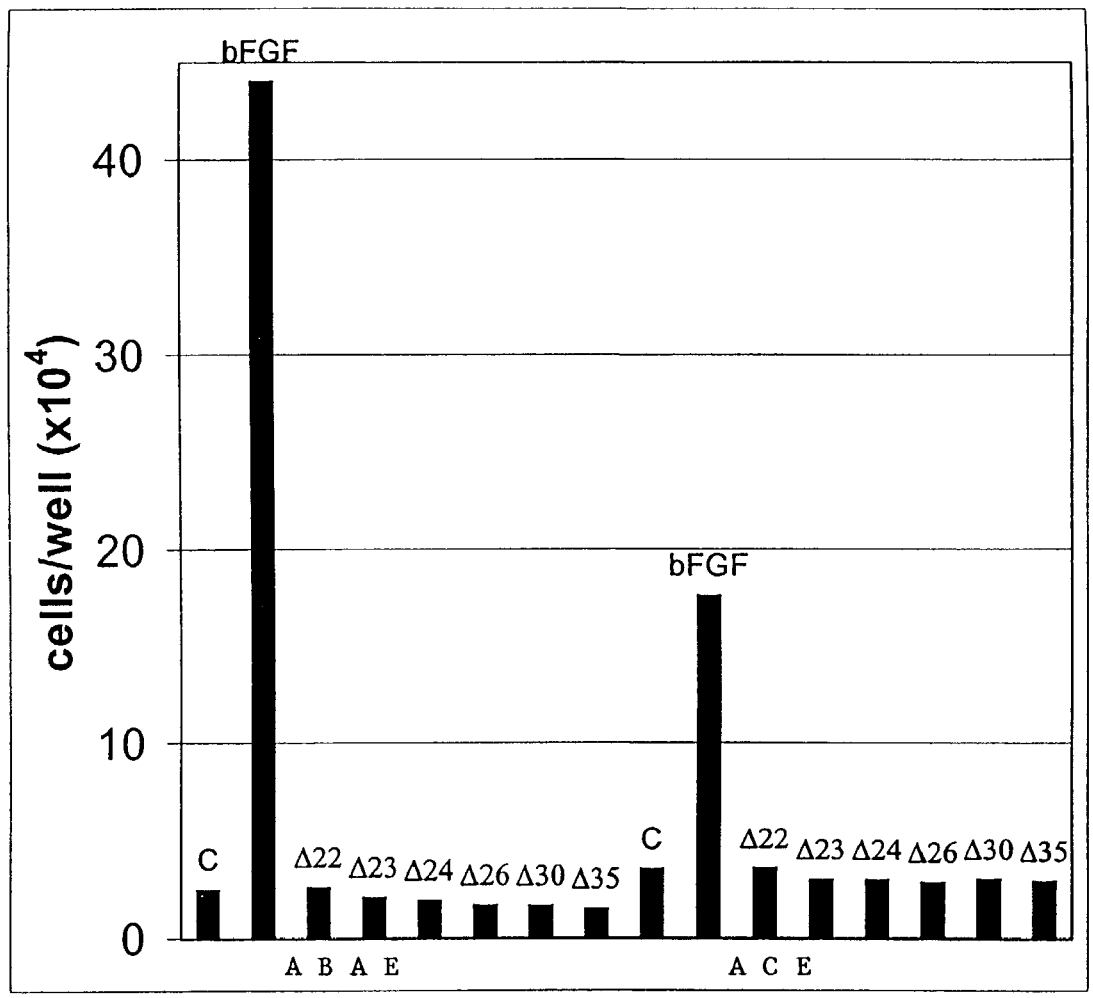
FIG. 3 shows the results of experiments where various truncated KGF molecules were tested on vascular endothelial cells derived from either the bovine aortic arch (adult bovine aortic endothelial cells (ABAE), left side of figure) or from the bovine adrenal gland capillaries (adrenal cortex-derived capillary endothelial cells (ACE), right side of figure). The histograms show the final cell density of cultures exposed to saturating concentrations of the various KGF polypeptides, or basic FGF (bFGF), after seven days in culture.

It should be noted that $KGF_{des1-35}$ which retained only 2-3% of the biological activity of the native form, was as active as aFGF when tested on Balb/Mk cells. Since this form is more homologous to aFGF than any of the other truncations, the question was raised as to whether this truncated form of KGF might have lost the target cell specificity peculiar to KGF. As explained above, KGF only stimulates cells of epithelial origin in contrast to other forms of FGF which have a wide range of target cells, and endothelial cells in particular. However, this apparently does not occur since when tested on either adrenal cortex-derived capillary endothelial cells (ACE) or adult bovine aortic endothelial cells (ABAE) cells (see below), in the presence or absence of heparin, $KGF_{des1-35}$, as well as other shorter truncations, were inactive (FIG. 3).

TABLE 1

Mitogenic Activity of KGF Polypeptides

| KGF Polypeptide | Average % Relative Activity (per unit weight basis)* | MW of $KGF_{xxx}$** | Average % Relative Activity (on a per molecule basis) |
|---|---|---|---|
| Full Length ($KGF_{163}$) | 100 | 18882 | 100 |
| $KGF_{des1-15}$ | 154 | 17229 | 141 |
| $KGF_{des1-18}$ | 166 | 16958 | 149 |

TABLE 1-continued

Mitogenic Activity of KGF Polypeptides

| KGF Polypeptide | Average % Relative Activity (per unit weight basis)* | MW of KGF$_{xxx}$** | Average % Relative Activity (on a per molecule basis) |
|---|---|---|---|
| KGF$_{des1-19}$ | 100 | 16829 | 89 |
| KGF$_{des1-20}$ | 187 | 16673 | 165 |
| KGF$_{des1-21}$ | 200 | 16536 | 175 |
| KGF$_{des1-22}$ | 600 | 16435 | 522 |
| KGF$_{des1-23}$ | 1000 | 16278 | 862 |
| KGF$_{des1-24}$ | 1000 | 16191 | 857 |
| KGF$_{des1-25}$ | 150 | 16028 | 127 |
| KGF$_{des1-26}$ | 100 | 15913 | 84 |
| KGF$_{des1-30}$ | 28.5 | 15433 | 23 |
| KGF$_{des1-35}$ | 3 | 14892 | 2 |

*ED$_{50}$ of (KGF$_{xxx}$ ÷ KGF$_{163}$) × 100
**Molecular weight (MW) was calculated using the Vector NTI program (Dec. 22, 1999), Infomax, Inc.

The activity of an analog of KGF$_{des1-22}$, with an alanine substituted for the naturally occurring N-terminal arginine, expressed in E. coli, was compared to an E. coli-expressed KGF$_{des1-23}$. The analog was tested multiple times and showed an ED$_{50}$ similar to that of E. coli-expressed KGF$_{des1-23}$.

Example 5

KGF Bioactivity on ABAE or ACE Cells

KGF can be characterized by its lack of activity on vascular endothelial cells derived from large vessels (adult bovine aortic endothelial cells, ABAE) or capillary cells (adrenal cortex-derived capillary endothelial cells, ACE) as compared with other forms of FGF, such as basic FGF (bFGF) or acidic FGF (aFGF). To analyze whether the various truncated forms of FGF retained this cell specificity, their biological activity on endothelial cells was tested.

Stock cultures of ABAE and ACE cells were grown and maintained in Dulbecco's modified Eagle medium supplemented with 10% bovine serum, 0.25 µg/ml fungizone, and 2 ng/ml bFGF. The cells were incubated at 37° C. with a 10% CO$_2$ concentration and 99% humidity.

In the mitogenic assay, either 5×10$^3$ ABAE or ACE cells were plated per well in 12-well plates in stock culture medium, as described in Gospodarowicz et. al. *Proc. Natl. Acad. USA* (1976) 73:4120-4124; Gospodarowicz et. al. *J. Cell. Physiol.* (1976) 127:121-136; and Gospodarowicz et. al. *Proc. Natl. Acad. USA* (1989) 86:7311-7315.

Saturating concentrations of KGF$_{163}$, as well as the various truncated variants of KGF and basic FGF were added every other day. After 7 days in culture, cells were trypsinized as described for the Balb/MK cell cultures and the final cell density was determined using a Coulter counter.

As shown in FIG. 3, all of the tested N-terminally truncated KGF polypeptides lacked activity on both ABAE and ACE as compared with bFGF. The truncations were based, in part, on structure alignment with acidic FGF. The results confirm that the potency of native KGF can be changed to that of acidic FGF without changing cell specificity. Acidic FGF is a known mitogen for Balb/Mk cells and its potency is 10-fold less than that of KGF. This reflects its lower binding affinity for the KGF receptor. Removal of the first 30 to 35 amino acids of native KGF leads to the strong decrease in biological activity shown by those truncated analogs (28.5 and 3% that of native KGF). At the same time, the degree of homology between acidic FGF and KGF increases when cell structural determinants for interacting with the FGF receptor are kept. Thus, KGF analogs with longer deletions behave more like acidic FGF. Surprisingly, even with the longest deletion, the target cell specificity typical of KGF is kept and the analogs, in contrast with acidic FGF or basic FGF, are not mitogenic for vascular endothelial cells.

Example 6

Thermal Stability Studies

The ability of native KGF and various N-terminally truncated KGF polypeptides to withstand elevated temperatures was examined. Samples containing 0.1 mg/ml protein were prepared in Ca$^{++}$ Mg$^{++}$-free PBS and 100 µl of each sample was aliquoted into 1 ml plastic vials. The vials were sealed and placed in a 37° C. incubator. At predetermined time intervals, vials were withdrawn and analyzed for the loss of soluble proteins.

30 µl aliquots were analyzed by SDS-PAGE electrophoresis. SDS-PAGE was performed on an electrophoresis system (Novex, San Diego, Calif., U.S.A.) using Tris-glycine precast gels (5% to 20% acrylamide, according to the method of Laemmli *Nature* (1970) 227:680-685). Samples were mixed with reducing or non-reducing SDS sample buffer without heating before loading.

The proteins were detected by Coomassie blue staining. The stained gels were scanned by densitometry using a BioRad Model GS 700 Imaging densitometer (Richmond, Calif., USA). The amount of soluble protein was determined by integrating the stained-band area and plotting the result as a function of time of incubation at 37° C. The half-life for the loss of soluble monomeric protein was then estimated from these kinetic curves.

The biological activity of the samples at various time intervals was also determined using the Balb/Mk cell proliferation assay as described above. The half-life for biological activity of the various samples was determined by plotting the ED$_{50}$ of the samples as a function of time of incubation at 37° C.

In particular, the thermal stability and oligomer formation of native KGF (KGF$_{163}$) verses KGF$_{des1-23}$ was assessed by incubating the KGF polypeptides (184 µg/ml native KGF and 138 µg/ml KGF$_{des1-23}$, diluted in PBS) for periods ranging from 0 to 8 days at 37° C. Aliquots were taken daily and their potency assessed on Balb/Mk cells, while oligomer formation was assessed by SDS-PAGE. When analyzed by SDS-PAGE, native KGF formed dimers readily. Dimerization was far less evident for KGF$_{des1-23}$. Also striking was the decrease in staining as a function of time for the monomeric form of native KGF. Again, this was far less evident for KGF$_{des1-23}$.

The cell proliferation assay indicated that under these conditions, the biological half-life of native KGF was 2 days while that of KGF$_{des1-23}$ was 7 days.

Figure 4:
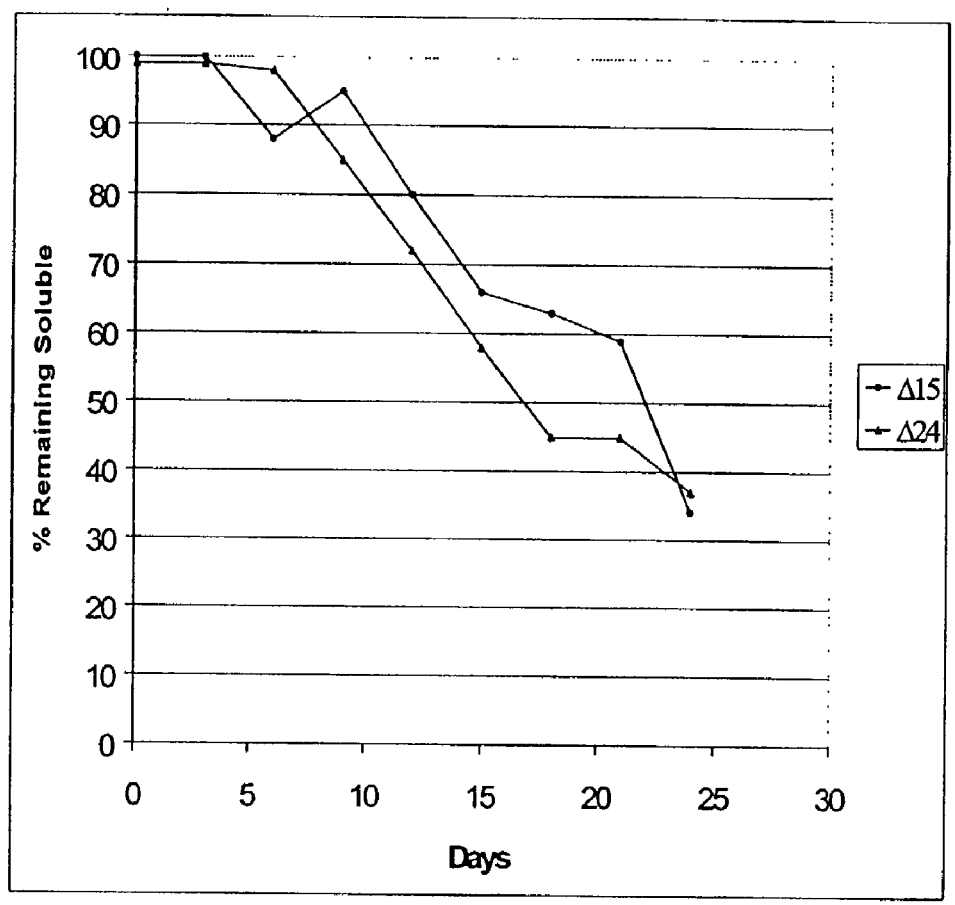
FIG. 4 shows the amount of soluble $KGF_{des1-24}$ (▲) and $KGF_{des1-15}$ (●), determined by SDS-PAGE as a function of time of incubation at 37° C.

Thermal stability studies also indicated that KGF$_{des1-15}$, KGF$_{des1-18}$, KGF$_{des1-19}$, KGF$_{des1-20}$, KGF$_{des1-21}$, KGF$_{des1-22}$, KGF$_{des1-24}$, KGF$_{des1-25}$, KGF$_{des1-26}$, KGF$_{des1-30}$ were more stable than the full-length KGF, although by varying degrees. A typical stability study which lasted 24 days with samples taken every 3 days is shown in FIG. 4. In this study, KGF$_{des1-24}$ and KGF$_{des1-15}$ (100 µg/ml) were diluted in PBS and incubated at 37° C. Samples were analyzed under non-reducing conditions by SDS-PAGE. Gels were then stained and scanned by densitometry.

Figure 5:
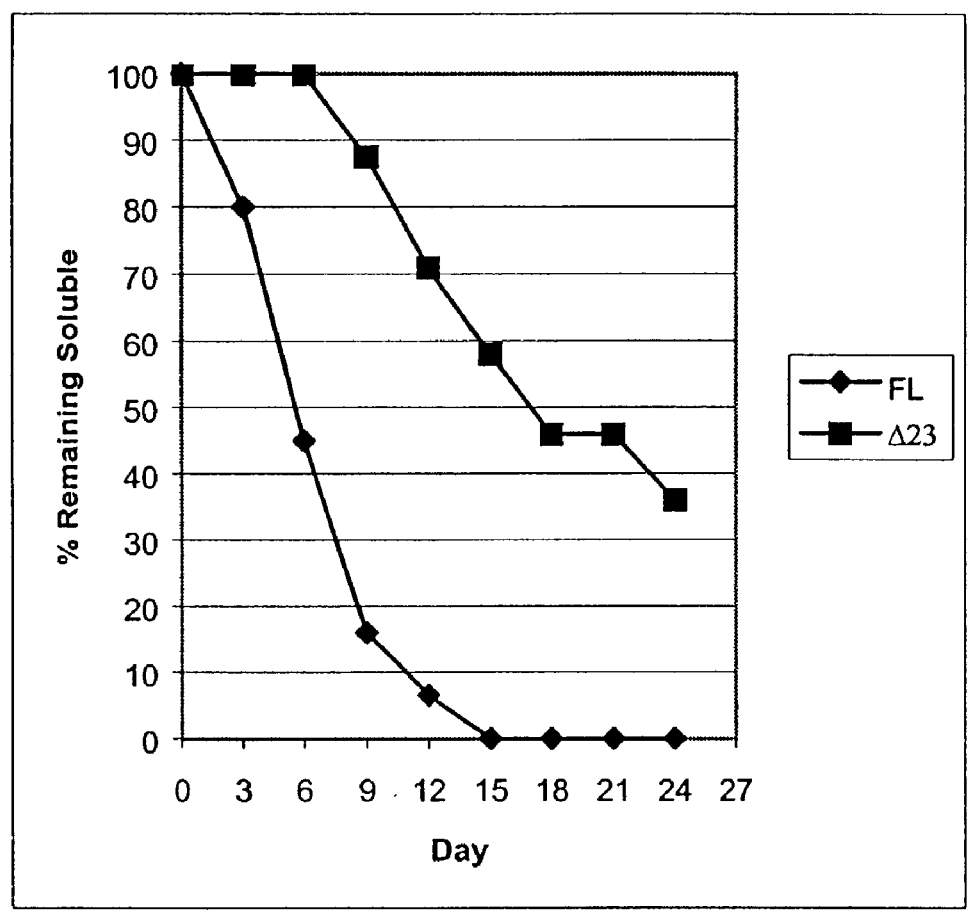
FIG. 5 shows the amount of soluble $KGF_{des1-23}$ (■) and native KGF (FL, ◆) determined by SDS-PAGE as a function of time of incubation at 37° C.

Extension of the thermal stability studies from 9 days to 24 days permitted a more accurately defined half-life solution of $KGF_{des1-23}$ versus native KGF. As shown in FIG. 5, the half-life of native KGF was 7 days versus 17 days for $KGF_{des1-23}$.

These results, taken together, indicate that the difference in biological activity between native KGF and the truncated molecules might be caused, in part, by differing thermal stability.

Example 7

Acid Stability at pH 2.1

To follow the formation of oligomer as a function of time, native KGF and $KGF_{des1-23}$ samples, maintained for various time intervals at 37° C., were analyzed by reverse phase HPLC. 100 µl samples were diluted to 1 ml in 0. 1% trifluoroacetic acid (TFA) in water, pH 2.1. The sample was then applied to a Vydac $C_4$ column (0.46 cm×25 cm, 5 µm particle size, 300 A° pore size) equilibrated in 0.1% (v/v) TFA. Protein was eluted with a linear 115 min multilinear acetonitrile gradient in (20-100%). The absorbance peaks were analyzed for their protein content by integrating their surface area. The amount of monomeric protein was plotted as a function of time. The half-life for the monomeric protein was then estimated as described above. To determine the formation of oligomers, samples were also analyzed under non-reducing conditions by SDS-PAGE. Biological activity of the various protein peaks was also determined using the Balb/Mk cell proliferation assay as described above.

Figure 6:
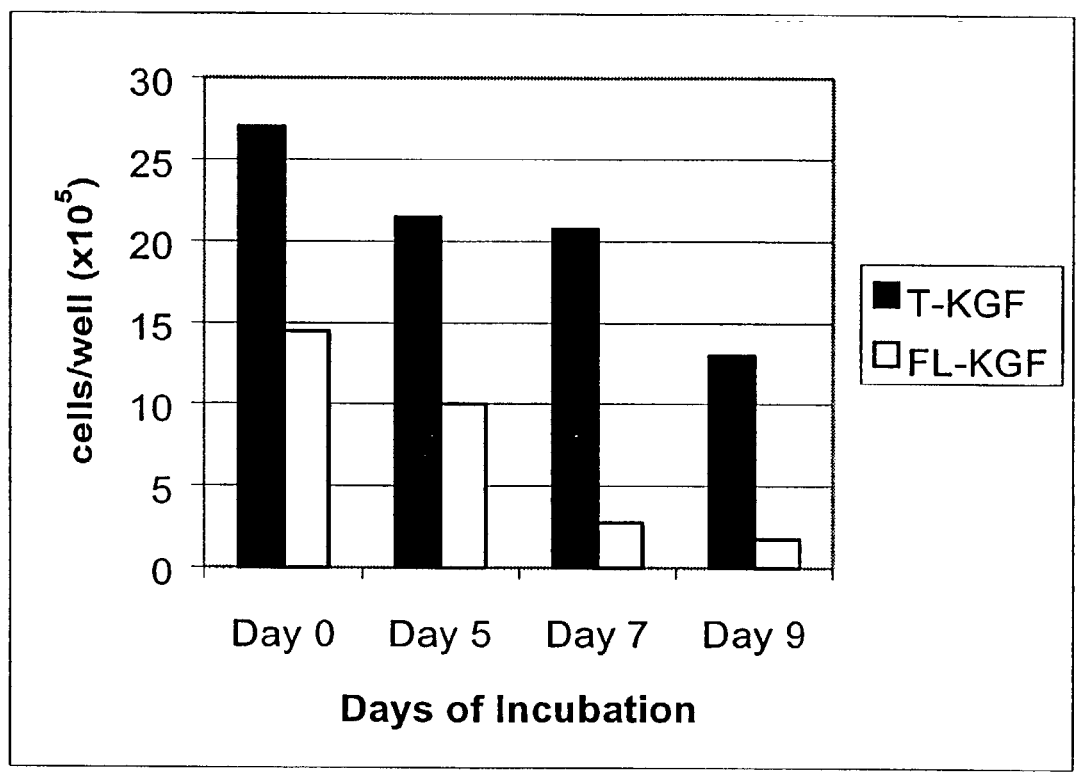
FIG. 6 depicts the results of the thermal and acid stability test described in the examples. FL-KGF represents $KGF_{163}$. T-KGF represents $KGF_{des1-23}$. The histograms represent the final cell density of the cultures after seven days when exposed to either saturating concentrations of $KGF_{des1-23}$ or $KGF_{163}$.

In particular, native KGF (28 µg/ml) and $KGF_{des1-23}$ (36 µmg/ml) were diluted in PBS and incubated for periods of time ranging from 0 to 9 days at 37° C. and aliquots were analyzed daily by reverse phase high pressure liquid chromatography (RP-HPLC) under acid conditions (pH 2.1). A single peak of UV absorbance was observed which eluted at 60 minutes for both native and $KGF_{des1-23}$. The intensity of the peak decreased as a function of time. However, the decrease was far more pronounced for native KGF than $KGF_{des1-23}$, so that by day 9, integration of both peaks indicated that the amount of native KGF was one-third that of $KGF_{des1-23}$. The decrease in mass of native KGF was associated with a drastic decrease in biological activity. By day 7, native KGF had become inactive. In contrast, $KGF_{des1-23}$ still retained 50% of its original biological activity (FIG. 6).

Example 8

Figure 7:
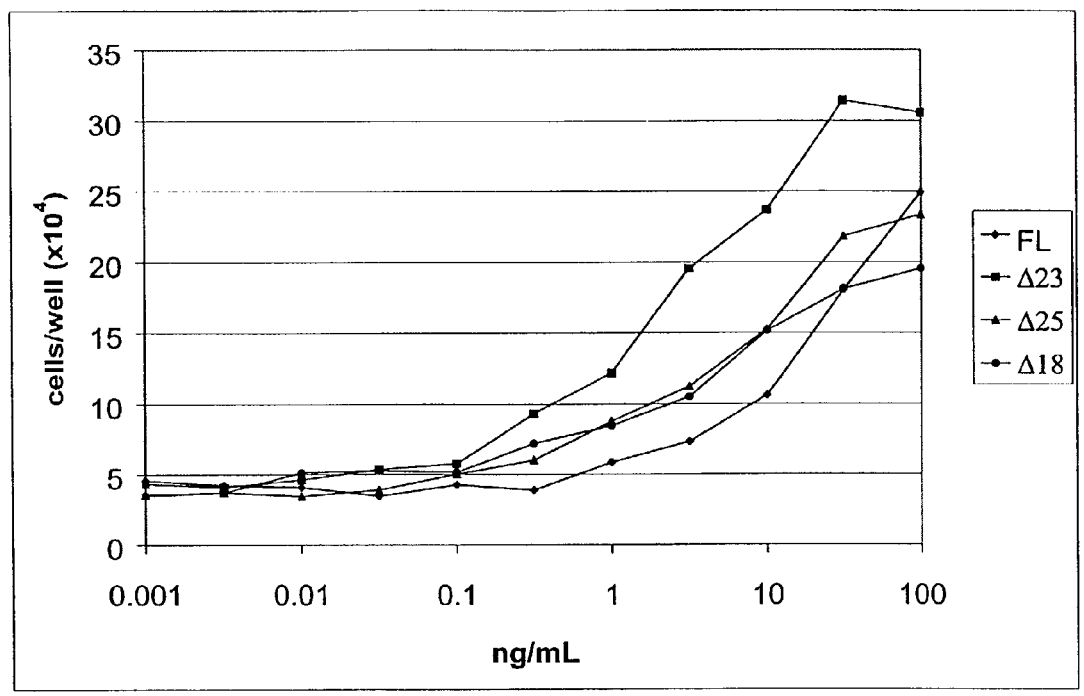
FIG. 7 shows the effect of increasing concentrations of native KGF (FL, ◆) and $KGF_{des1-18}$ (●), $KGF_{des1-23}$ (■) and $KGF_{des1-25}$ (▲) on the proliferation of Balb/Mk cells when added only once.

Comparison of the Bioactivity of Native KGF Versus $KGF_{des1-23}$ when Added Only Once Versus Every Other Day In the cell proliferation assay described above, increasing concentrations of native KGF and $KGF_{des1-23}$ were added every other day. If stability is the mechanism for enhanced activity, there should still be the same difference in dose response when native KGF or truncated KGF polypeptides are added once, rather than every other day, even though overall cell proliferation is less. To test this hypothesis, varying concentrations of $KGF_{des1-18}$, $KGF_{des1-23}$ and $KGF_{des1-25}$ were added only once, in the concentrations shown in FIG. 7. As shown in FIG. 7 and Table 2, the same difference in biological activity was observed with $KGF_{des1-23}$. In particular, $KGF_{des1-23}$ was 13-fold more active than native KGF when added once, versus 10-fold more active when added every other day. Additionally, both the $KGF_{des1-18}$ and $KGF_{des1-25}$ polypeptides showed an increase in activity over native KGF. This confirms that increased stability is one of the mechanisms which contributes to increased potency.

TABLE 2

Comparison of the Biological Activity of Native Versus Truncated KGFs Added Either Once or Every Other Day

| | Average % Activity | |
|---|---|---|
| KGF Polypeptide | Added Once | Added Every Other Day |
| Full Length | 100 | 100 |
| $KGF_{des1-18}$ | 173 | 150 |
| $KGF_{des1-23}$ | 1320 | 1000 |
| $KGF_{des1-25}$ | 173 | 160 |

Example 9

Is Protease Contamination Responsible for the Rapid Disappearance of Native KGF

To rule out the possibility that protease contamination of the native KGF preparation, absent from the $KGF_{des1-23}$ preparation, was responsible for the rapid disappearance of native KGF, the following experiment was done. Native KGF and $KGF_{des1-23}$ (100 µg/ml) were diluted in PBS and incubated at 37° C. either alone or mixed at an equal ratio (v/v). Samples were taken on day 3, 6, 9 and 12 and analyzed by SDS-PAGE, as described above. After staining, the gels were scanned by densitometry. If the native KGF disappeared and $KGF_{des1-23}$ did not, protease contamination would be ruled out.

Native KGF disappeared by day 6. However, $KGF_{des1-23}$ could still be seen after 12 days, eliminating the possibility of protease contamination as a reason for the disappearance of native KGF. Surprising however, was the difference in the band-staining intensity when $KGF_{des1-23}$ was incubated alone versus incubated in combination with native KGF. The staining intensity of the $KGF_{des1-23}$ band was far greater when incubated alone than when mixed with the native KGF. It is possible that when $KGF_{des1-23}$ is incubated with native KGF, complexes form and $KGF_{des1-23}$ is taken out of solution.

When the biological activity of native KGF versus $KGF_{des1-23}$ was analyzed, a 10-fold increase in potency was observed which correlated with greater thermal stability of the truncated form versus the native form. Thus, increased stability could in part explain the increased potency. This however does not appear to be the only mechanism contributing to increased activity. Without being bound by a particular theory, the lack of activity of native KGF may be due to precipitation out of solution. When various truncations above were analyzed for stability and biological activity, they showed increased stability and biological activity as compared to the native form. However, there was little correlation between increased stability and increased biological activity. For example, $KGF_{des1-15}$ and $KGF_{des1-24}$ had comparable thermal stability but $KGF_{des1-24}$ was 10-fold more potent than native KGF while $KGF_{des1-15}$ was 1.5-fold more active. Therefore other mechanisms likely exist which contribute to the increased potency of the most potent molecules, $KGF_{des1-22}$, $KGF_{des1-23}$, and $KGF_{des1-24}$. It is also remarkable that the domain conferring maximum increase in potency is limited, consisting of three residues. These three residues may therefore provide optimum conformation of KGF in its interaction with the receptor.

Truncation confirms that the potency of native KGF can be changed to that of aFGF without changing cell specificity. Acidic FGF is a known mitogen for Balb/Mk cells and it is 10-fold less active than KGF. This is due to its lower binding affinity for the KGF receptor. Removal of the first 30 to 35 amino acids led to a strong decrease in biological activity of the truncated polypeptides (28.5% and 3%, respectively, of native KGF). At the same time, the longer deletions increase the degree of homology between aFGF and KGF and increase cell structural determinants for interacting with the FGF receptor. Thus, the longer the deletions, the more like aFGF the truncated KGF polypeptides behave. Surprisingly, even the longest deletion retained the target cell specificity typical of KGF, i.e., for cells of epithelial origin, and the shortest polypeptides, in contrast with aFGF or bFGF, were not mitogenic for vascular endothelial cells. These findings, that the $NH_2$ terminal domain of KGF does not seem to be involved in its cell specificity, at least as far as the first 35 residues are concerned, are in contrast with earlier reports (see, e.g., International Publication No. WO 90/08771).

Example 10

In Vivo Efficacy of N-Terminally Truncated KGF Polypeptides

Full-length KGF ($KGF_{163}$) and an N-terminally truncated molecule, $KGF_{des1-23}$, were tested in a rat model of healing of a surgical colonic anastamosis. In particular, KGF formulations, containing 5 mg/ml $KGF_{163}$ or 1 mg/ml $KGF_{des1-23}$ were administered intraperitoneally to rats. Colonic crypt depth (in μm), a measure of cellular proliferation related to healing, and busting pressure in mm mercury, a measure of strength of the healed wound, were measured on days 2, 4 and 7 for rats given $KGF_{163}$ and on days 2, 4 and 6 for rats given the truncated molecule. Results are shown in Tables 3 and 4.

In particular, 1 mg/ml of the truncated molecule was as effective or more effective than 5 mg/ml of full-length KGF in promoting wound healing. Smaller doses of the truncated molecule were also effective. Based on these results, it is likely that other N-terminally truncated KGFs, particularly $KGF_{des1-22}$ and $KGF_{des1-24}$, are also as effective, if not more effective, for wound healing using smaller doses than that required using $KGF_{163}$.

TABLE 3

| Colonic Crypt Depth in μm, Expressed as Percent of Vehicle Control | | |
|---|---|---|
| Day Measured | Full Length KGF, 5 mg/kg | Truncated KGF, 1 mg/kg |
| 2 | 127 | 176 |
| 4 | 125 | 129 |
| 7 | 154 | 138 |
| (6 of $KGF_{des1-23}$) | | |

TABLE 4

| Bursting Pressure in mm Hg, Expressed as Percent of Vehicle Control | | |
|---|---|---|
| Day Measured | Full Length KGF, 5 mg/kg | Truncated KGF, 1 mg/kg |
| 2 | 134 | 163 |
| 4 | 149 | 151 |
| 7 | 119 | 148 |
| (6 of $KGF_{des1-23}$) | | |

Thus, novel KGF compositions and methods for using the same are disclosed. Although preferred embodiments of the subject invention have been described in some detail, it is understood that obvious variations can be made without departing from the spirit and the scope of the invention as defined by the appended claims.

We claim:

1. A composition comprising:
   (a) a therapeutically effective amount of a KGF polypeptide, wherein said KGF polypeptide is selected from the group consisting of:
      (i) a biologically active analog of $KGF_{des1-22}$, wherein said biologically active analog consists of the contiguous amino acid sequence depicted at amino acid residues 23-163, inclusive, of SEQ ID NO:26 with the N-terminal arginine residue substituted with an alanine residue and optionally with up to 7 other amino acid substitutions; and
      (ii) the polypeptide of (i), consisting of the amino acid sequence of (i), and an additional N-terminal methionine,
   wherein said KGF polypeptide exhibits an increase in bioactivity relative to mature, full-length, KGF ($KGF_{163}$) as determined by the Balb/MK bioactivity assay and specifically stimulates epithelial cell proliferation, and further wherein the therapeutically effective amount is 75% or less of the amount on a per molecule basis of $KGF_{163}$ needed to elicit an equivalent therapeutic response; and
   (b) a pharmaceutically acceptable excipient.

2. The composition of claim 1, wherein said biologically active analog consists of the contiguous amino acid sequence depicted at amino acid residues 23-163, inclusive, of SEQ ID NO:26 with the N-terminal arginine residue substituted with an alanine residue.

3. The composition of claim 1, wherein the therapeutically effective amount is 10% to 50% of the amount on a per molecule basis of the amount of $KGF_{163}$ needed to elicit an equivalent therapeutic response.

4. The composition of claim 1, wherein the therapeutically effective amount is 10% to 25% of the amount on a per molecule basis of the amount of $KGF_{163}$ needed to elicit an equivalent therapeutic response.

5. The composition of claim 1, wherein the therapeutically effective amount is 10% to 20% of the amount on a per molecule basis of the amount of $KGF_{163}$ needed to elicit an equivalent therapeutic response.

6. A method of stimulating epithelial cell proliferation comprising contacting epithelial cells with a composition according to claim 1.

7. The method of claim 6, wherein said biologically active analog consists of the contiguous amino acid sequence depicted at amino acid residues 23-163, inclusive, of SEQ ID NO:26 with the N-terminal arginine residue substituted with an alanine residue.

8. The method of claim 6, wherein the therapeutically effective amount is 10% to 50% of the amount on a per molecule basis of the amount of $KGF_{163}$ needed to elicit an equivalent therapeutic response.

9. The method of claim 6, wherein the therapeutically effective amount is 10% to 25% of the amount on a per molecule basis of the amount of $KGF_{163}$ needed to elicit an equivalent therapeutic response.

10. The method of claim 6, wherein the therapeutically effective amount is 10% to 20% of the amount on a per molecule basis of the amount of $KGF_{163}$ needed to elicit an equivalent therapeutic response.

11. The method of claim 6, wherein said contacting is done in vitro.

12. The method of claim 6, wherein said contacting is done in vivo.

13. A method of treating wounds comprising applying a KGF polypeptide composition according to claim 1 to an area of a wound to be treated and allowing the wound to heal.

14. The method of claim 13, wherein said biologically active analog consists of the contiguous amino acid sequence depicted at amino acid residues 23-163, inclusive, of SEQ ID NO:26 with the N-terminal arginine residue substituted with an alanine residue.

15. The method of claim 13, wherein the therapeutically effective amount is 10% to 50% of the amount on a per molecule basis of the amount of $KGF_{163}$ needed to elicit an equivalent therapeutic response.

16. The method of claim 13, wherein the therapeutically effective amount is 10% to 25% of the amount on a per molecule basis of the amount of $KGF_{163}$ needed to elicit an equivalent therapeutic response.

17. The method of claim 13, wherein the therapeutically effective amount is 10% to 20% of the amount on a per molecule basis of the amount of $KGF_{163}$ needed to elicit an equivalent therapeutic response.

18. The method of claim 13, wherein said contacting is done in vitro.

19. The method of claim 13, wherein said contacting is done in vivo.

* * * * *

SEQUENCE LISTING

<160> NUMBER OF SEQ ID NOS: 28

<210> SEQ ID NO 1
<211> LENGTH: 94
<212> TYPE: DNA
<213> ORGANISM: Artificial Sequence
<220> FEATURE:
<223> OTHER INFORMATION: Description of Artificial Sequence:  Oligo 1
      for KGF-des1-15
<220> FEATURE:
<221> NAME/KEY: misc_feature
<222> LOCATION: (1)
<223> OTHER INFORMATION: wherein the 5' C has a 5' phosphate group

<400> SEQUENCE: 1
catgagcagc cctgagcgac acacaagaag ttatgattac atggaaggag gggatataag      60
agtgagaaga ctcttctgtc gaacacagtg gtac                                  94

<210> SEQ ID NO 2
<211> LENGTH: 86
<212> TYPE: DNA

```
<213> ORGANISM: Artificial Sequence
<220> FEATURE:
<223> OTHER INFORMATION: Description of Artificial Sequence: Oligo 2
      for KGF-des1-15
<220> FEATURE:
<221> NAME/KEY: misc_feature
<222> LOCATION: (1)
<223> OTHER INFORMATION: wherein the 5' C has a 5' phosphate group

<400> SEQUENCE: 2
cactgtgttc gacagaagag tcttctcact cttatatccc ctccttccat gtaatcataa     60
cttcttgtgt gtcgctcagg gctgct                                          86

<210> SEQ ID NO 3
<211> LENGTH: 85
<212> TYPE: DNA
<213> ORGANISM: Artificial Sequence
<220> FEATURE:
<223> OTHER INFORMATION: Description of Artificial Sequence: Oligo 1
      for KGF-des1-18
<220> FEATURE:
<221> NAME/KEY: misc_feature
<222> LOCATION: (1)
<223> OTHER INFORMATION: wherein the 5' C has a 5' phosphate group

<400> SEQUENCE: 3
catggagcga cacacaagaa gttatgatta catggaagga ggggatataa gagtgagaag     60
actcttctgt cgaacacagt ggtac                                           85

<210> SEQ ID NO 4
<211> LENGTH: 77
<212> TYPE: DNA
<213> ORGANISM: Artificial Sequence
<220> FEATURE:
<223> OTHER INFORMATION: Description of Artificial Sequence: Oligo 2
      for KGF-des1-18
<220> FEATURE:
<221> NAME/KEY: misc_feature
<222> LOCATION: (1)
<223> OTHER INFORMATION: wherein the 5' C has a 5' phosphate group

<400> SEQUENCE: 4
cactgtgttc gacagaagag tcttctcact cttatatccc ctccttccat gtaatcataa     60
cttcttgtgt gtcgctc                                                    77

<210> SEQ ID NO 5
<211> LENGTH: 82
<212> TYPE: DNA
<213> ORGANISM: Artificial Sequence
<220> FEATURE:
<223> OTHER INFORMATION: Description of Artificial Sequence: Oligo 1
      for KGF-des1-19
<220> FEATURE:
<221> NAME/KEY: misc_feature
<222> LOCATION: (1)
<223> OTHER INFORMATION: wherein the 5' C has a 5' phosphate group

<400> SEQUENCE: 5
catgcgacac acaagaagtt atgattacat ggaaggaggg gatataagag tgagaagact     60
cttctgtcga acacagtggt ac                                              82

<210> SEQ ID NO 6
<211> LENGTH: 74
<212> TYPE: DNA
<213> ORGANISM: Artificial Sequence
<220> FEATURE:
<223> OTHER INFORMATION: Description of Artificial Sequence: Oligo 2
```

```
        for KGF-des1-19
<220> FEATURE:
<221> NAME/KEY: misc_feature
<222> LOCATION: (1)
<223> OTHER INFORMATION: wherein the 5' C has a 5' phosphate group

<400> SEQUENCE: 6
cactgtgttc gacagaagag tcttctcact cttatatccc ctccttccat gtaatcataa      60
cttcttgtgt gtcg                                                       74

<210> SEQ ID NO 7
<211> LENGTH: 79
<212> TYPE: DNA
<213> ORGANISM: Artificial Sequence
<220> FEATURE:
<223> OTHER INFORMATION: Description of Artificial Sequence:  Oligo 1
        for KGF-des1-20
<220> FEATURE:
<221> NAME/KEY: misc_feature
<222> LOCATION: (1)
<223> OTHER INFORMATION: wherein the 5' C has a 5' phosphate group

<400> SEQUENCE: 7
catgcacaca agaagttatg attacatgga aggaggggat ataagagtga gaagactctt      60
ctgtcgaaca cagtggtac                                                  79

<210> SEQ ID NO 8
<211> LENGTH: 71
<212> TYPE: DNA
<213> ORGANISM: Artificial Sequence
<220> FEATURE:
<223> OTHER INFORMATION: Description of Artificial Sequence:  Oligo 2
        for KGF-des1-20
<220> FEATURE:
<221> NAME/KEY: misc_feature
<222> LOCATION: (1)
<223> OTHER INFORMATION: wherein the 5' C has a 5' phosphate group

<400> SEQUENCE: 8
cactgtgttc gacagaagag tcttctcact cttatatccc ctccttccat gtaatcataa      60
cttcttgtgt g                                                          71

<210> SEQ ID NO 9
<211> LENGTH: 76
<212> TYPE: DNA
<213> ORGANISM: Artificial Sequence
<220> FEATURE:
<223> OTHER INFORMATION: Description of Artificial Sequence:  Oligo 1
        for KGF-des1-21
<220> FEATURE:
<221> NAME/KEY: misc_feature
<222> LOCATION: (1)
<223> OTHER INFORMATION: wherein the 5' C has a 5' phosphate group

<400> SEQUENCE: 9
catgaccaga agttatgatt acatggaagg aggggatata agagtgagaa gactcttctg      60
tcgaacacag tggtac                                                     76

<210> SEQ ID NO 10
<211> LENGTH: 68
<212> TYPE: DNA
<213> ORGANISM: Artificial Sequence
<220> FEATURE:
<223> OTHER INFORMATION: Description of Artificial Sequence:  Oligo 2
        for KGF-des1-21
<220> FEATURE:
<221> NAME/KEY: misc_feature
```

```
<222> LOCATION: (1)
<223> OTHER INFORMATION: wherein the 5' C has a 5' phosphate group

<400> SEQUENCE: 10
cactgtgttc gacagaagag tcttctcact cttatatccc ctccttccat gtaatcataa      60
cttctggt                                                              68

<210> SEQ ID NO 11
<211> LENGTH: 73
<212> TYPE: DNA
<213> ORGANISM: Artificial Sequence
<220> FEATURE:
<223> OTHER INFORMATION: Description of Artificial Sequence:  Oligo 1
      for KGF-des1-22
<220> FEATURE:
<221> NAME/KEY: misc_feature
<222> LOCATION: (1)
<223> OTHER INFORMATION: wherein the 5' C has a 5' phosphate group

<400> SEQUENCE: 11
catgagaagt tatgattaca tggaaggagg ggatataaga gtgagaagac tcttctgtcg      60
aacacagtgg tac                                                        73

<210> SEQ ID NO 12
<211> LENGTH: 65
<212> TYPE: DNA
<213> ORGANISM: Artificial Sequence
<220> FEATURE:
<223> OTHER INFORMATION: Description of Artificial Sequence:  Oligo 2
      for KGF-des1-22
<220> FEATURE:
<221> NAME/KEY: misc_feature
<222> LOCATION: (1)
<223> OTHER INFORMATION: wherein the 5' C has a 5' phosphate group

<400> SEQUENCE: 12
cactgtgttc gacagaagag tcttctcact cttatatccc ctccttccat gtaatcataa      60
cttct                                                                 65

<210> SEQ ID NO 13
<211> LENGTH: 67
<212> TYPE: DNA
<213> ORGANISM: Artificial Sequence
<220> FEATURE:
<223> OTHER INFORMATION: Description of Artificial Sequence:  Oligo 1
      for KGF-des1-24
<220> FEATURE:
<221> NAME/KEY: misc_feature
<222> LOCATION: (1)
<223> OTHER INFORMATION: wherein the 5' C has a 5' phosphate group

<400> SEQUENCE: 13
catgtatgat tacatggaag gagggatat aagagtgaga agactcttct gtcgaacaca       60
gtggtac                                                               67

<210> SEQ ID NO 14
<211> LENGTH: 59
<212> TYPE: DNA
<213> ORGANISM: Artificial Sequence
<220> FEATURE:
<223> OTHER INFORMATION: Description of Artificial Sequence:  Oligo 2
      for KGF-des1-24
<220> FEATURE:
<221> NAME/KEY: misc_feature
<222> LOCATION: (1)
<223> OTHER INFORMATION: wherein the 5' C has a 5' phosphate group
```

-continued

```
<400> SEQUENCE: 14
cactgtgttc gacagaagag tcttctcact cttatatccc ctccttccat gtaatcata        59

<210> SEQ ID NO 15
<211> LENGTH: 64
<212> TYPE: DNA
<213> ORGANISM: Artificial Sequence
<220> FEATURE:
<223> OTHER INFORMATION: Description of Artificial Sequence: Oligo 1
      for KGF-des1-25
<220> FEATURE:
<221> NAME/KEY: misc_feature
<222> LOCATION: (1)
<223> OTHER INFORMATION: wherein the 5' C has a 5' phosphate group

<400> SEQUENCE: 15
catggattac atggaaggag gggatataag agtgagaaga ctcttctgtc gaacacagtg        60
gtac                                                                    64

<210> SEQ ID NO 16
<211> LENGTH: 56
<212> TYPE: DNA
<213> ORGANISM: Artificial Sequence
<220> FEATURE:
<223> OTHER INFORMATION: Description of Artificial Sequence: Oligo 2
      for KGF-des1-25
<220> FEATURE:
<221> NAME/KEY: misc_feature
<222> LOCATION: (1)
<223> OTHER INFORMATION: wherein the 5' C has a 5' phosphate group

<400> SEQUENCE: 16
cactgtgttc gacagaagag tcttctcact cttatatccc ctccttccat gtaatc           56

<210> SEQ ID NO 17
<211> LENGTH: 61
<212> TYPE: DNA
<213> ORGANISM: Artificial Sequence
<220> FEATURE:
<223> OTHER INFORMATION: Description of Artificial Sequence: Oligo 1
      for KGF-des1-26
<220> FEATURE:
<221> NAME/KEY: misc_feature
<222> LOCATION: (1)
<223> OTHER INFORMATION: wherein the 5' C has a 5' phosphate group

<400> SEQUENCE: 17
catgtacatg gaaggagggg atataagagt gagaagactc ttctgtcgaa cacagtggta       60
c                                                                       61

<210> SEQ ID NO 18
<211> LENGTH: 53
<212> TYPE: DNA
<213> ORGANISM: Artificial Sequence
<220> FEATURE:
<223> OTHER INFORMATION: Description of Artificial Sequence: Oligo 2
      for KGF-des1-26
<220> FEATURE:
<221> NAME/KEY: misc_feature
<222> LOCATION: (1)
<223> OTHER INFORMATION: wherein the 5' C has a 5' phosphate group

<400> SEQUENCE: 18
cactgtgttc gacagaagag tcttctcact cttatatccc ctccttccat gta              53

<210> SEQ ID NO 19
<211> LENGTH: 49
```

```
<210> SEQ ID NO 19
<211> LENGTH: 49
<212> TYPE: DNA
<213> ORGANISM: Artificial Sequence
<220> FEATURE:
<223> OTHER INFORMATION: Description of Artificial Sequence: Oligo1
      for KGF-des1-30
<220> FEATURE:
<221> NAME/KEY: misc_feature
<222> LOCATION: (1)
<223> OTHER INFORMATION: wherein the 5' C has a 5' phosphate group

<400> SEQUENCE: 19
catgggggat ataagagtga aagactctt ctgtcgaaca cagtggtac                49

<210> SEQ ID NO 20
<211> LENGTH: 41
<212> TYPE: DNA
<213> ORGANISM: Artificial Sequence
<220> FEATURE:
<223> OTHER INFORMATION: Description of Artificial Sequence: Oligo 2
      for KGF-des1-30
<220> FEATURE:
<221> NAME/KEY: misc_feature
<222> LOCATION: (1)
<223> OTHER INFORMATION: wherein the 5' C has a 5' phosphate group

<400> SEQUENCE: 20
cactgtgttc gacagaagag tcttctcact cttatatccc c                       41

<210> SEQ ID NO 21
<211> LENGTH: 34
<212> TYPE: DNA
<213> ORGANISM: Artificial Sequence
<220> FEATURE:
<223> OTHER INFORMATION: Description of Artificial Sequence: Oligo 1
      for KGF-des1-35
<220> FEATURE:
<221> NAME/KEY: misc_feature
<222> LOCATION: (1)
<223> OTHER INFORMATION: wherein the 5' C has a 5' phosphate group

<400> SEQUENCE: 21
catgagaaga ctcttctgtc gaacacagtg gtac                               34

<210> SEQ ID NO 22
<211> LENGTH: 26
<212> TYPE: DNA
<213> ORGANISM: Artificial Sequence
<220> FEATURE:
<223> OTHER INFORMATION: Description of Artificial Sequence: Oligo 2
      for KGF-des1-35
<220> FEATURE:
<221> NAME/KEY: misc_feature
<222> LOCATION: (1)
<223> OTHER INFORMATION: wherein the 5' C has a 5' phosphate group

<400> SEQUENCE: 22
cactgtgttc gacagaagag tcttct                                        26

<210> SEQ ID NO 23
<211> LENGTH: 28
<212> TYPE: DNA
<213> ORGANISM: Artificial Sequence
<220> FEATURE:
<223> OTHER INFORMATION: Description of Artificial Sequence: Oligo 1
      for KGF-des1-37
<220> FEATURE:
<221> NAME/KEY: misc_feature
<222> LOCATION: (1)
<223> OTHER INFORMATION: wherein the 5' C has a 5' phosphate group

<400> SEQUENCE: 23
```

```
catgctcttc tgtcgaacac agtggtac                                28
```

```
<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Oligo 2
      for KGF-des1-37
<220> FEATURE:
<221> NAME/KEY: misc_feature
<222> LOCATION: (1)
<223> OTHER INFORMATION: wherein the 5' C has a 5' phosphate group

<400> SEQUENCE: 24
cactgtgttc gacagaagag                                         20

<210> SEQ ID NO 25
<211> LENGTH: 489
<212> TYPE: DNA
<213> ORGANISM: Artificial Sequence
<220> FEATURE:
<223> OTHER INFORMATION: Description of Artificial Sequence: DNA
      encoding KGF-163
<220> FEATURE:
<221> NAME/KEY: CDS
<222> LOCATION: (1)..(489)

<400> SEQUENCE: 25
```

```
tgc aat gac atg act cca gag caa atg gct aca aat gtg aac tgt tcc    48
Cys Asn Asp Met Thr Pro Glu Gln Met Ala Thr Asn Val Asn Cys Ser
 1               5                  10                  15 agc cct gag cga cac aca aga agt tat gat tac atg gaa gga ggg gat    96
Ser Pro Glu Arg His Thr Arg Ser Tyr Asp Tyr Met Glu Gly Gly Asp
             20                  25                  30 ata aga gtg aga aga ctc ttc tgt cga aca cag tgg tac ctg agg atc   144
Ile Arg Val Arg Arg Leu Phe Cys Arg Thr Gln Trp Tyr Leu Arg Ile
         35                  40                  45 gat aaa aga ggc aaa gta aaa ggg acc caa gag atg aag aat aat tac   192
Asp Lys Arg Gly Lys Val Lys Gly Thr Gln Glu Met Lys Asn Asn Tyr
 50                  55                  60 aat atc atg gaa atc agg aca gtg gca gtt gga att gtg gca atc aaa   240
Asn Ile Met Glu Ile Arg Thr Val Ala Val Gly Ile Val Ala Ile Lys
 65                  70                  75                  80 ggg gtg gaa agt gaa ttc tat ctt gca atg aac aag gaa gga aaa ctc   288
Gly Val Glu Ser Glu Phe Tyr Leu Ala Met Asn Lys Glu Gly Lys Leu
                 85                  90                  95 tat gca aag aaa gaa tgc aat gaa gat tgt aac ttc aaa gaa cta att   336
Tyr Ala Lys Lys Glu Cys Asn Glu Asp Cys Asn Phe Lys Glu Leu Ile
            100                 105                 110 ctg gaa aac cat tac aac aca tat gca tca gct aaa tgg aca cac aac   384
Leu Glu Asn His Tyr Asn Thr Tyr Ala Ser Ala Lys Trp Thr His Asn
        115                 120                 125 gga ggg gaa atg ttt gtt gcc tta aat caa aag ggg att cct gta aga   432
Gly Gly Glu Met Phe Val Ala Leu Asn Gln Lys Gly Ile Pro Val Arg
    130                 135                 140 gga aaa aaa acg aag aaa gaa caa aaa aca gcc cac ttt ctt cct atg   480
Gly Lys Lys Thr Lys Lys Glu Gln Lys Thr Ala His Phe Leu Pro Met
145                 150                 155                 160 gca ata act                                                       489
Ala Ile Thr

<210> SEQ ID NO 26
```

<211> LENGTH: 163
<212> TYPE: PRT
<213> ORGANISM: Artificial Sequence
<220> FEATURE:
<223> OTHER INFORMATION: Description of Artificial Sequence: DNA encoding KGF-163

<400> SEQUENCE: 26

```
Cys Asn Asp Met Thr Pro Glu Gln Met Ala Thr Asn Val Asn Cys Ser
  1               5                  10                  15

Ser Pro Glu Arg His Thr Arg Ser Tyr Asp Tyr Met Glu Gly Gly Asp
                 20                  25                  30

Ile Arg Val Arg Arg Leu Phe Cys Arg Thr Gln Trp Tyr Leu Arg Ile
             35                  40                  45

Asp Lys Arg Gly Lys Val Lys Gly Thr Gln Glu Met Lys Asn Asn Tyr
         50                  55                  60

Asn Ile Met Glu Ile Arg Thr Val Ala Val Gly Ile Val Ala Ile Lys
 65                  70                  75                  80

Gly Val Glu Ser Glu Phe Tyr Leu Ala Met Asn Lys Glu Gly Lys Leu
                 85                  90                  95

Tyr Ala Lys Lys Glu Cys Asn Glu Asp Cys Asn Phe Lys Glu Leu Ile
                100                 105                 110

Leu Glu Asn His Tyr Asn Thr Tyr Ala Ser Ala Lys Trp Thr His Asn
             115                 120                 125

Gly Gly Glu Met Phe Val Ala Leu Asn Gln Lys Gly Ile Pro Val Arg
         130                 135                 140

Gly Lys Lys Thr Lys Lys Glu Gln Lys Thr Ala His Phe Leu Pro Met
145                 150                 155                 160

Ala Ile Thr
```

<210> SEQ ID NO 27
<211> LENGTH: 423
<212> TYPE: DNA
<213> ORGANISM: Artificial Sequence
<220> FEATURE:
<223> OTHER INFORMATION: Description of Artificial Sequence: DNA encoding KGF-des1-22 (with the N-terminal arginine residue substituted with an alanine residue)
<220> FEATURE:
<221> NAME/KEY: CDS
<222> LOCATION: (1)..(423)

<400> SEQUENCE: 27

```
gct agt tat gat tac atg gaa gga ggg gat ata aga gtg aga aga ctc      48
Ala Ser Tyr Asp Tyr Met Glu Gly Gly Asp Ile Arg Val Arg Arg Leu
  1               5                  10                  15 ttc tgt cga aca cag tgg tac ctg agg atc gat aaa aga ggc aaa gta      96
Phe Cys Arg Thr Gln Trp Tyr Leu Arg Ile Asp Lys Arg Gly Lys Val
                 20                  25                  30 aaa ggg acc caa gag atg aag aat aat tac aat atc atg gaa atc agg     144
Lys Gly Thr Gln Glu Met Lys Asn Asn Tyr Asn Ile Met Glu Ile Arg
             35                  40                  45 aca gtg gca gtt gga att gtg gca atc aaa ggg gtg gaa agt gaa ttc     192
Thr Val Ala Val Gly Ile Val Ala Ile Lys Gly Val Glu Ser Glu Phe
         50                  55                  60 tat ctt gca atg aac aag gaa gga aaa ctc tat gca aag aaa gaa tgc     240
Tyr Leu Ala Met Asn Lys Glu Gly Lys Leu Tyr Ala Lys Lys Glu Cys
 65                  70                  75                  80 aat gaa gat tgt aac ttc aaa gaa cta att ctg gaa aac cat tac aac     288
Asn Glu Asp Cys Asn Phe Lys Glu Leu Ile Leu Glu Asn His Tyr Asn
                 85                  90                  95
```

```
aca tat gca tca gct aaa tgg aca cac aac gga ggg gaa atg ttt gtt       336
Thr Tyr Ala Ser Ala Lys Trp Thr His Asn Gly Gly Glu Met Phe Val
        100                 105                 110 gcc tta aat caa aag ggg att cct gta aga gga aaa aaa acg aag aaa       384
Ala Leu Asn Gln Lys Gly Ile Pro Val Arg Gly Lys Lys Thr Lys Lys
            115                 120                 125 gaa caa aaa aca gcc cac ttt ctt cct atg gca ata act                   423
Glu Gln Lys Thr Ala His Phe Leu Pro Met Ala Ile Thr
        130                 135                 140

<210> SEQ ID NO 28
<211> LENGTH: 141
<212> TYPE: PRT
<213> ORGANISM: Artificial Sequence
<220> FEATURE:
<223> OTHER INFORMATION: Description of Artificial Sequence: DNA
      encoding KGF-des1-22 (with the N-terminal arginine residue
      substituted with an alanine residue)

<400> SEQUENCE: 28

Ala Ser Tyr Asp Tyr Met Glu Gly Gly Asp Ile Arg Val Arg Arg Leu
 1               5                  10                  15

Phe Cys Arg Thr Gln Trp Tyr Leu Arg Ile Asp Lys Arg Gly Lys Val
            20                  25                  30

Lys Gly Thr Gln Glu Met Lys Asn Asn Tyr Asn Ile Met Glu Ile Arg
        35                  40                  45

Thr Val Ala Val Gly Ile Val Ala Ile Lys Gly Val Glu Ser Glu Phe
    50                  55                  60

Tyr Leu Ala Met Asn Lys Glu Gly Lys Leu Tyr Ala Lys Lys Glu Cys
65                  70                  75                  80

Asn Glu Asp Cys Asn Phe Lys Glu Leu Ile Leu Glu Asn His Tyr Asn
                85                  90                  95

Thr Tyr Ala Ser Ala Lys Trp Thr His Asn Gly Gly Glu Met Phe Val
            100                 105                 110

Ala Leu Asn Gln Lys Gly Ile Pro Val Arg Gly Lys Lys Thr Lys Lys
            115                 120                 125

Glu Gln Lys Thr Ala His Phe Leu Pro Met Ala Ile Thr
        130                 135                 140
```